(12) United States Patent  
Wang et al.

(10) Patent No.: US 9,416,181 B2  
(45) Date of Patent: Aug. 16, 2016

(54) COMPOSITIONS FOR CELL CULTURE AND METHODS OF USING THE SAME

(71) Applicant: AbbVie Inc., North Chicago, IL (US)

(72) Inventors: Min Wang, Shrewsbury, MA (US); Patrick M. Hossler, Westborough, MA (US); Sean W. McDermott, Warwick, RI (US); Christopher Racicot, Auburn, MA (US); Kofi Chemfe, Worcester, MA (US); John Fann, Shrewsbury, MA (US)

(73) Assignee: AbbVie Inc., North Chicago, IL (US)

( * ) Notice: Subject to any disclaimer, the term of this patent is extended or adjusted under 35 U.S.C. 154(b) by 4 days.

(21) Appl. No.: 14/270,675

(22) Filed: May 6, 2014

(65) Prior Publication Data

US 2014/0329279 A1     Nov. 6, 2014

Related U.S. Application Data

(60) Provisional application No. 61/819,839, filed on May 6, 2013.

(51) Int. Cl.
| | |
|---|---|
| *C12N 5/00* | (2006.01) |
| *C07K 16/24* | (2006.01) |
| *A61K 39/395* | (2006.01) |
| *C07K 16/00* | (2006.01) |

(52) U.S. Cl.
CPC .......... *C07K 16/241* (2013.01); *A61K 39/39591* (2013.01); *C07K 16/00* (2013.01); *C12N 5/005* (2013.01); *C12N 5/0043* (2013.01); *C07K 2317/14* (2013.01); *C12N 2501/999* (2013.01); *C12N 2510/02* (2013.01)

(58) Field of Classification Search
CPC ... A61K 8/97; A61K 2800/522; A61K 8/602; A61K 31/353; A61K 31/7048; C12N 2510/02; C12N 2511/00; C12N 5/0018; C12N 5/0031; C12N 5/0037; C12P 21/00; C12P 21/005
See application file for complete search history.

(56) References Cited

U.S. PATENT DOCUMENTS

| | | | |
|---|---|---|---|
| 4,554,101 A | 11/1985 | Hopp | |
| 4,885,244 A * | 12/1989 | Miyamori et al. | ............ 435/101 |
| 6,090,382 A | 7/2000 | Salfeld et al. | |
| 6,369,294 B1 * | 4/2002 | Piedrahita et al. | ............ 800/14 |
| 2005/0064521 A1 * | 3/2005 | Yang et al. | ............ 435/7.23 |
| 2005/0089882 A1 | 4/2005 | Gressel et al. | |
| 2008/0274507 A1 | 11/2008 | Gomes et al. | |
| 2009/0004247 A1 * | 1/2009 | Kosuna et al. | ............ 424/439 |
| 2009/0311253 A1 | 12/2009 | Ghayur et al. | |
| 2010/0136636 A1 * | 6/2010 | Takemoto | ............ 435/125 |
| 2011/0030098 A1 | 2/2011 | Jugde et al. | |
| 2011/0091876 A1 | 4/2011 | Presnell et al. | |
| 2011/0256544 A1 | 10/2011 | Kolodkin et al. | |
| 2012/0264105 A1 | 10/2012 | Rozeboom | |
| 2014/0275486 A1 | 9/2014 | Chumsae | |
| 2014/0314779 A1 * | 10/2014 | Vijayasankaran et al. | ............ 424/141.1 |

FOREIGN PATENT DOCUMENTS

WO    WO 2012/147053    11/2012

OTHER PUBLICATIONS

Liu, H., et al., Heterogeneity of monoclonal antibodies. J Pharm Sci, 2008. 97(7): p. 2426-47.
Du, Y., et al., Chromatographic analysis of the acidic and basic species of recombinant monoclonal antibodies. MAbs, 2012. 4(5): p. 578-85.
Pardridge, W.M., et al., Cationized hyperimmune immunoglobulins: pharmacokinetics, toxicity evaluation and treatment of human immunodeficiency virus-infected human-peripheral blood lymphocytes-severe combined immune deficiency mice. J Pharmacol Exp Ther, 1996. 276(1): p. 246-52.
Huang, L., et al., In vivo deamidation characterization of monoclonal antibody by LC/MS/MS. Anal Chem, 2005. 77(5): p. 1432-9.
Vlasak, J., et al., Identification and characterization of asparagine deamidation in the light chain CDR1 of a humanized IgG1 antibody. Anal Biochem, 2009. 392(2): p. 145-54.
Banks, D.D., et al., The effect of sucrose hydrolysis on the stability of protein therapeutics during accelerated formulation studies. J Pharm Sci, 2009. 98(12): p. 4501-10.
Khawli, L.A., et al., Charge variants in IgG1: Isolation, characterization, in vitro binding properties and pharmacokinetics in rats. MAbs, 2010. 2(6): p. 613-24.
Abu-Absi, S.F., et al., Defining process design space for monoclonal antibody cell culture. Biotechnol Bioeng, 2010. 106(6): p. 894-905.
Lambert, J.D. and R.J. Elias, The antioxidant and pro-oxidant activities of green tea polyphenols: a role in cancer prevention. Arch Biochem Biophys, 2010. 501(1): p. 65-72.
Forester, S.C. and J.D. Lambert, The role of antioxidant versus pro-oxidant effects of green tea polyphenols in cancer prevention. Mol Nutr Food Res, 2011. 55(6): p. 844-54.
Halliwell, B., Are polyphenols antioxidants or pro-oxidants? What do we learn from cell culture and in vivo studies? Arch Biochem Biophys, 2008. 476(2): p. 107-12.
Bellion, P., et al., Formation of hydrogen peroxide in cell culture media by apple polyphenols and its effect on antioxidant biomarkers in the colon cell line HT-29. Mol Nutr Food Res, 2009. 53(10): p. 1226-36.

(Continued)

*Primary Examiner* — Daniel C Gamett
(74) *Attorney, Agent, or Firm* — Lathrop & Gage LLP

(57) ABSTRACT

Supplementation of the bioflavonoids such as epigallocatechin gallate, rutin, naringin, or genistein into mammalian cell culture media are shown to be effective in reduction of acidic species variants on recombinant antibodies. The demonstrated reduction in acidic species through the use of bioflavonoids, facilitates the manufacturing of a less heterogeneous product with potential improvements in antibody structure and function.

22 Claims, 18 Drawing Sheets

(56) References Cited

OTHER PUBLICATIONS

Long, L.H., M.V. Clement, and B. Halliwell, Artifacts in cell culture: rapid generation of hydrogen peroxide on addition of (−)-epigallocatechin, (−)-epigallocatechin gallate, (+)-catechin, and quercetin to commonly used cell culture media. Biochem Biophys Res Commun, 2000. 273(1): p. 50-3.

Wu, C., et al., Simultaneous targeting of multiple disease mediators by a dual-variable-domain immunoglobulin. Nat Biotechnol, 2007. 25(11): p. 1290-7.

Klaunig, J.E., L.M. Kamendulis, and B.A. Hocevar, Oxidative stress and oxidative damage in carcinogenesis. Toxicol Pathol, 2010. 38(1): p. 96-109.

Zhou, L. and R.J. Elias, Factors influencing the antioxidant and pro-oxidant activity of polyphenols in oil-in-water emulsions. J Agric Food Chem, 2012. 60(11): p. 2906-15.

National Center for Biotechnology Information. PubChem Compound Database; CID=5280805. Available from: https://pubchem.ncbi.nlm.nih.gov/summary/summary.cgi?cid=5280805&loc=ec_rcs (Accessed Apr. 18, 2014), 23 pages.

National Center for Biotechnology Information. PubChem Compound Database; CID=442428. Available from: https://pubchem.ncbi.nlm.nih.gov/summary/summary.cgi?cid=442428&loc=ec_rcs (Accessed Apr. 18, 2014), 19 pages.

National Center for Biotechnology Information. PubChem Compound Database; CID=5280961. Available from: https://pubchem.ncbi.nlm.nih.gov/summary/summary.cgi?cid=5280961&loc=ec_rcs (Accessed Apr. 18, 2014), 61 pages.

National Center for Biotechnology Information. PubChem Compound Database; CID=65064. Available from: https://pubchem.ncbi.nlm.nih.gov/summary/summary.cgi?cid=65064&loc=ec_rcs (Accessed Apr. 18, 2014), 22 pages.

PCT/US2014/036908 International Search Report & Written Opinion mailed Sep. 20, 2014, 10 pages.

* cited by examiner

A

B

COMPOSITIONS FOR CELL CULTURE AND METHODS OF USING THE SAME

RELATED APPLICATION

This application claims priority to U.S. Provisional Patent Application No. 61/819,839, filed May 6, 2013, which is incorporated by reference into the present application in its entirety and for all purposes.

FIELD OF THE INVENTION

This disclosure relates to production of recombinant proteins. More particularly, this disclosure relates to compositions and methods for reducing charge variant of recombinant monoclonal antibodies when expressed in a cell culture.

BACKGROUND

Biologics have been widely used as human therapeutics. Many biologics are produced as recombinant proteins in cell cultures. Charge variants may occur in such recombinant proteins due to post-translational modifications, among others. Charge variants of a recombinant protein may affect the stability, activity, immunogenicity, and pharmacokinetics of the recombinant protein. More particularly, monoclonal antibodies have a wide range of acidic species variants, including those associated with the addition of covalent adducts as well as the chemical degradation at specific peptide regions on the antibody. These variants play an important role in the overall heterogeneity of recombinant therapeutic proteins and are typically monitored during their manufacturing to ensure they fall within regulatory limits.

Heterogeneity may be caused by different types of post-translational modifications. For review, see Walsh, 2006 and Liu, 2008. Heterogeneity manifested as charge variants is often observed in recombinantly expressed proteins. Charge variants may result from chemical degradations (e.g., oxidation, deamidation, isomerization, fragmentation) or addition reactions (e.g., glycation adducts, or covalent additions) that may occur at various locations on the proteins. The cumulative effect of these molecular events is structural and conformational changes on the protein molecule, which may, in turn, change the isoelectric point (pI) of the protein, and may even affect the protein's function. For instance, acidic species variants are likely to bestow a net negative charge on the protein, or they may remove additional positive charges. For review, see Du, 2012.

Numerous protein variants caused by acidic species have been reported. While some of these variants only have a nominal impact on the affected protein, others have more profound effects on the functions of the protein. It has been postulated that the degree of impact of a particular charge variant is dependent on where on the protein the impact occurred, and the extent to which the protein has been modified. Changes to the $F_c$ region of an antibody may not be as impactful as changes occurring on the $F_{ab}$ region, where target binding occurs (Du, 2012). Charge variants have been shown to affect the in vitro and in vivo binding characteristics of antibodies (Pardridge, 1994, Pardridge, 1996). Asparagine deamidation has been shown to cause a significant decrease in antigen binding (Vlasak, 2009, Huang, 2005). Glycation has been shown to increase the formation of aggregates (Banks, 2009). Moreover, acidic species have been shown to cause a lower $F_cR_n$ binding response, even though the in vivo PK appeared unaffected (Khawli, 2010). Taken together, the presence of acidic species variants in therapeutic proteins may potentially impact the efficacy and/or function of the affected proteins.

Various studies have been conducted to determine how acidic species variants are dependent upon the local environment in which the proteins are produced, as well as the environment in which they are stored after purification. Abu Absi et al. described that higher cell culture temperature facilitates an increase in the amount of deamidated species in the recombinant protein expressed. See Abu Absi et al. (2010). However, no data have been reported on the effects of cell culture media on the resulting product quality of recombinant antibodies.

SUMMARY

This disclosure advances the art by providing composition and methods for reducing charge variants of recombinant monoclonal antibodies when expressed in a cell culture. The disclosure also provides methods for reducing the amount of these charge variant species without substantially compromising the overall yield or quality of the antibody production.

Many therapeutic proteins, such as monoclonal antibodies, are produced by cultured mammalian cells containing one or more polynucleotides encoding the proteins. Several acidic species resulting from posttranslational modifications have been reported for some recombinant monoclonal antibodies when chemically defined media (CDM) is used in the cell culture media. It is disclosed here that supplementation of one or more bioflavonoids (or flavonoids) into mammalian cell culture feed media significantly decreases the overall levels of acidic species variants on the recombinant proteins (e.g., monoclonal antibodies) produced by cultured cells.

In one embodiment, a method is disclosed which includes culturing a plurality of cells in a culture medium containing one or more bioflavonoid, wherein at least one of the plurality of cells contains a polynucleotide encoding the polypeptide. In another embodiment, the culture medium is a CDM. In another embodiment, the one or more bioflavonoids may be added into a CDM as a supplement by a used prior to use for culturing cells. In another embodiment, the one or more bioflavonoids may be added into a CDM at the site of manufacturing as a pre-mixed liquid medium. The pre-mixed liquid medium may be prepared as a working solution or as a concentrate to be diluted by a user prior to use. Alternatively, the one or more bioflavonoids may be added into a CDM at the site of manufacturing as a pre-mixed solid medium which may be reconstituted by an end user prior to use.

The disclosed composition may be used for culturing many different cell types, for example, mammalian cells, insect cells, among others. In one embodiment, the cells are host cells into which one or more foreign genes (or transgenes) have been introduced. In one aspect, the one or more transgenes may be integrated onto the chromosomes of the host cells. In another aspect, the one or more transgenes may exist outside of the host chromosomes, such as in a vector that is capable of propagating independently of the host chromosomes. These transgenic cells are capable of expressing a one or more recombinant proteins.

In another embodiment, the recombinant protein is an antibody. In one aspect, the recombinant protein is an anti-TNF-alpha monoclonal antibody. See U.S. Pat. No. 6,090,382, which is hereby incorporated by reference into this disclosure in its entirety. In another aspect, the anti-TNF-alpha antibody expressed in the cell culture has been modified. See U.S. patent application Ser. No. 14/078,181 filed Nov. 12, 2013, which is hereby incorporated by reference into this disclosure in its entirety. In another aspect, the recombinant protein is an antibody that contains more than one variable domains, for example, one that contains dual variable domains (DVD).

In another embodiment, a culture medium for culturing a host cell is disclosed which contains one or more bioflavonoids in an amount that is non-toxic to the host cell but effective in reducing the acidic species of recombinant proteins produced by the host cell. In one aspect, the disclosed composition, when supplemented to a host cell culture expressing anti-TNF-alpha antibody, is capable of reducing acidic species of the anti-TNF-alpha antibody by at least 40%, 50%, 60%, 80%, 90% or even by as much as 100%, as compared to anti-TNF-alpha antibody produced in cell culture without the composition. The term "non-toxic" means the supplement does not significantly reduce cell viability, cell growth or production of the recombinant protein.

In another embodiment, one or more bioflavonoids may be supplemented to a cell culture medium to help reduce charge variants of the recombinant proteins. In one aspect, the levels of charge variants in a recombinant protein produced with CDM in the absence of bioflavonoids may be measured to determine if there is a need for bioflavonoids supplementation. In another aspect, the levels of charge variants in a recombinant protein produced with CDM supplemented with bioflavonoids may be measured to assess the effects of the bioflavonoids on reducing charge variants in the proteins.

In one embodiment, no significant amount (i.e., no more than trace amount) of manganese is added or included in the CDM. In another embodiment, the culture medium may include any other necessary or desirable ingredients known in the art, such as carbohydrates, including glucose, essential and/or non-essential amino acids, lipids and lipid precursors, nucleic acid precursors, vitamins, inorganic salts, trace elements including rare metals, and/or cell growth factors. In another embodiment, the culture medium is a chemically defined medium with supplementation of one or more bioflavonoids.

Example of the bioflavonoids may be one or more members selected from the group consisting of epigallocatechin gallate (EGCG), rutin, naringin, genistein and combination thereof. In one aspect, the bioflavonoid is epigallocatechin gallate (EGCG), and the working concentration of the epigallocatechin gallate when used in a liquid medium for culturing cells may be from 0.001 g/L to 0.2 g/L, from 0.01 g/L to 0.1 g/L, or from 0.05 g/L to 0.1 g/L. In another aspect, the bioflavonoid is rutin, and the working concentration of the rutin when used in a liquid medium for culturing cells may be from 0.001 g/L to 0.2 g/L, from 0.01 g/L to 0.1 g/L, or from 0.05 g/L to 0.1 g/L. In another aspect, the bioflavonoid is naringin, and the working concentration of the naringin when used in a liquid medium for culturing cells may be from 0.001 g/L to 2 g/L, from 0.01 g/L to 1 g/L, or from 0.05 g/L to 0.5 g/L. In another aspect, the bioflavonoid is genistein, and the working concentration of the genistein when used in a liquid medium for culturing cells may be from 0.001 g/L to 0.2 g/L, from 0.01 g/L to 0.1 g/L, or from 0.05 g/L to 0.1 g/L.

Bioflavonoid(s) may be obtained from plants or certain parts of a plant, such as a fruit. The bioflavonoid supplement of the present disclosure may be added to the culture medium in a substantially pure form or it may be in the form of a crude extract prepared from plants or plant parts. In another aspect, the bioflavonoids may be obtained from naturally existing microorganisms or from transgenic microorganisms that are engineered to produce the bioflavonoids.

DETAILED DESCRIPTION

Figure 1A:
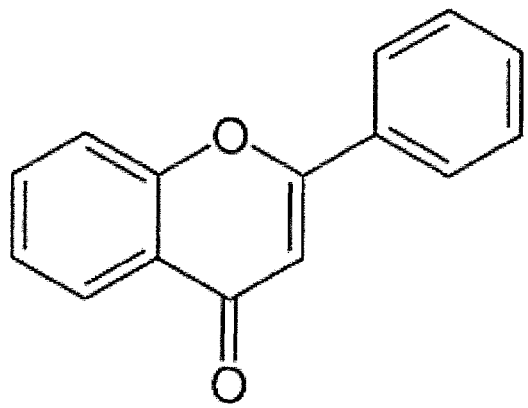
FIGS. 1A-1C show three main backbone structures of bioflavonoids (or flavonoids).

It is disclosed here that supplementation of bioflavonoids into mammalian cell culture feed media significantly reduces the overall levels of acidic species variants on recombinant monoclonal antibodies. Besides EGCG, other bioflavonoids, such as rutin, naringin, and genistein, are all effective in decreasing the overall levels of acidic species variants. These results suggest that the observed effects are likely due to a general feature of this class of molecules. These results are consistently observed at multiple concentrations, and across different cell culture scales. The decrease in acidic species variants may result in a concomitant increase in the main species, with no significant change on the basic species.

Bioflavonoids are commonly found in nature as a class of secondary plant metabolites in apples (Bellion, 2009), and green tea (Lambert, 2010). Bioflavonoids are considered safe for human consumption because they have low toxicity. Molecules in this family are associated with polyphenolic ring chemical structures and ketone groups. Bioflavonoids have been extensively studied to have both pro-oxidant and anti-oxidant activity in vitro. Bioflavonoids have been demonstrated to scavenge a wide range of reactive oxygen species (ROS), and reactive nitrogen species (RNS) (Halliwell, 2008). In addition, bioflavonoids have been shown to chelate metal ions, thus decreasing the pro-oxidant behavior of these metals (Halliwell, 2008).

Bioflavonoids, especially epigallocatechin gallate (EGCG), also have a well-known role of being pro-oxidants. The formation of these pro-oxidant byproducts are important because they may lead to more ROS (Bellion, 2009, Long, 2000). Formation of ROS and RNS in industrial mammalian cell culture is well expected because of the relatively high dissolved oxygen levels that are typically employed in these cultures (Halliwell, 2008). These baseline levels coupled to the additional amount from bioflavonoids can lead to even higher levels of ROS.

Under elevated oxidative stress conditions, mammalian cells respond by an oxidative stress response. In humans, the induction of antioxidant defense is designed to not remove all ROS, but to control their levels at manageable levels so as to manage the potential for oxidative damage (Halliwell, 2008). In cultured mammalian cells, a similar defense mechanism exists for managing the levels of ROS, as has been shown through the induction of the glutathione pathway (Bellion, 2009).

In the present disclosure, it is shown that the supplementation of various members of the bioflavonoid family of molecules facilitated a significant decrease in the overall levels of acidic species variants on a recombinant $IgG_1$ antibody. EGCG, rutin, naringin, and genistein are especially effective towards the overall reduction in acidic species. The principal mechanism for this reduction is likely through an overall reduction in ROS levels either through direct interaction of the bioflavonoids with ROS species present in the culture environment, and/or through the upregulation of the cellular oxidative stress response.

Figure 1B:
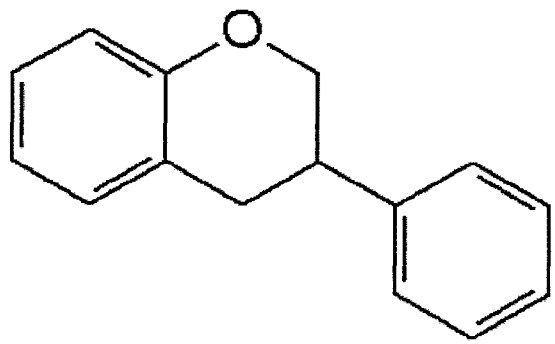
Figure 1C:
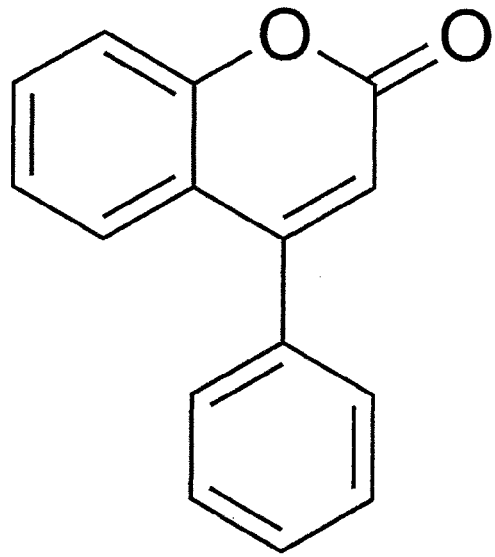
Figure 1D:
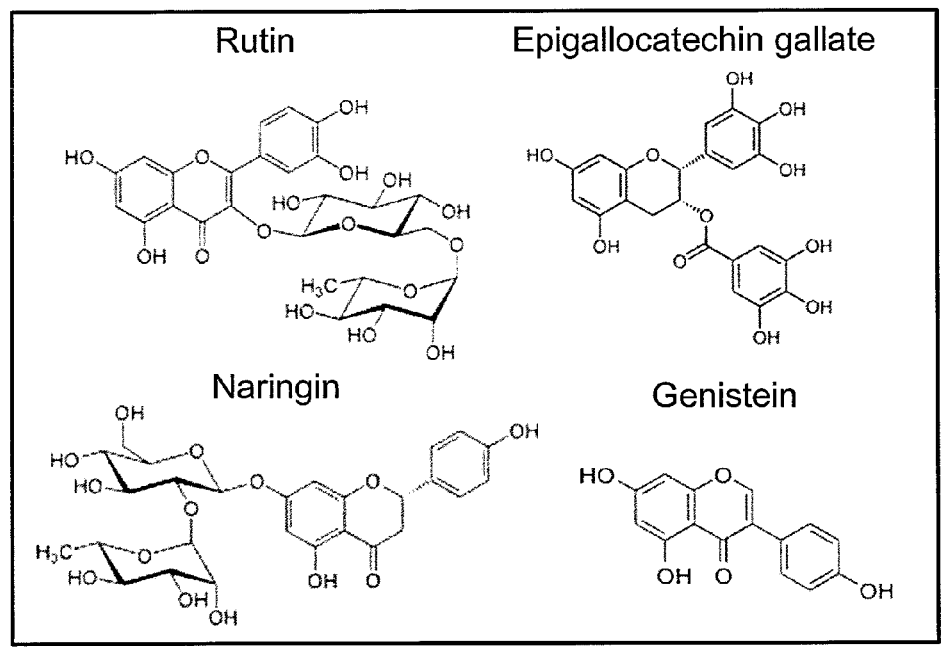
FIG. 1D shows the chemical structures of bioflavonoids utilized in the present disclosure.

For purpose of this disclosure, "bioflavonoid" refers to molecules having the backbone structures as depicted in FIG. 1A, 1B or 1C. It is to be understood that various groups may be added to these backbone structures and various substitutions may be made to arrive at different bioflavonoid molecules or derivatives thereof. Examples of bioflavonoids may include but are not limited to EGCG, rutin, naringin, genistein, quercetin, kaempferol, myricetin, fisetin, isorhamnetin, pachypodol, rhamnazin, luteolin, apigenin, tangeritin, hesperetin, eriodictyol, homoeriodictyol, taxifolin, dihydrokaempferol, daidzein, glycitein. By way of example, the specific structures of EGCG, rutin, naringin, and genistein are illustrated in FIG. 1D.

Four bioflavonoids, namely, EGCG, rutin, naringin, and genistein, do not have a significantly adverse impact on overall cell culture performance. However, when the concentrations of these bioflavonoids exceed certain level, lower cell growth are observed. In one embodiment, when EGCG concentration is higher than 0.1 g/L, the peak viable cell density begin to drop lower than the unsupplemented control condition. However, despite this overall lower cell growth, the cell viability remain higher than the control up to the point of culture harvest. As a result, the harvest titers are comparable between the supplemented cultures with EGCG and the unsupplemented cultures.

Flow cytometry results show a marked reduction of overall ROS level towards the end of the cultures in cultures supplemented with EGCG as compared to unsupplemented controls. It is unlikely that the reduction of ROS levels and the reduction of acidic species variants are merely coincidental. These results suggest a link between the overall ROS levels and the amount of acidic species variants on a recombinant protein.

It is shown here that supplementation of bioflavonoids into mammalian cell culture feed media is capable of significantly decreasing the overall levels of acidic species variants on multiple recombinant proteins, including but not limited to antibodies having one or more variable domains. Shake flask studies evaluating the feed media supplementation of EGCG and rutin were all effective in this regard, suggesting that this behavior is a feature of this class of molecules in general. These results were consistently observed at multiple concentrations, across different cell lines and cell culture scales, and in a statistically meaningful manner. The resulting decrease in acidic species variants facilitated a concomitant increase in the main species to a larger degree, and the basic species to a lesser degree.

In one aspect, the disclosed bioflavonoids do not show an adverse impact on overall cell culture performance over a wide range of concentrations. Once the concentrations of the bioflavonoids exceed a critical level, lower cell growth may result.

In another aspect, a combination of multiple bioflavonoid molecules may be used. These multiple bioflavonoid molecules may have a more effective and even synergistic impact in reducing acidic species charge variants. In another aspect, the disclosed bioflavonoid molecules may have the same or similar effects both in vitro in a cell line and in vivo in the body of a mammal.

Unless otherwise defined herein, scientific and technical terms used herein have the meanings that are commonly understood by those of ordinary skill in the art. In the event of any latent ambiguity, definitions provided herein take precedent over any dictionary or extrinsic definition. Unless otherwise required by context, singular terms shall include pluralities and plural terms shall include the singular. The use of "or" means "and/or" unless stated otherwise. The use of the term "including", as well as other forms, such as "includes" and "included", is not limiting.

Generally, nomenclatures used in connection with cell and tissue culture, molecular biology, immunology, microbiology, genetics and protein and nucleic acid chemistry and hybridization described herein are those well known and commonly used in the art. The methods and techniques provided herein are generally performed according to conventional methods well known in the art and as described in various general and more specific references that are cited and discussed throughout the present specification unless otherwise indicated. Enzymatic reactions and purification techniques are performed according to manufacturer's specifications, as commonly accomplished in the art or as described herein. The nomenclatures used in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

That the disclosure may be more readily understood, select terms are defined below.

The term "chemically defined media" (CDM), as known and used in the art, and as used herein, refers to media suitable for cell culture growth, wherein the media is free of plant-, fungal-, or animal-derived extracts, hydrolsates, or other mixtures of unknown composition. Chemically defined media can be distinguished from "serum-free media" in that chemically defined media may contain recombinant forms of plant-, fungal-, or animal-proteins (e.g., bovine, or human serum albumin), wherein the origin and composition of the proteins are biochemically known.

The term "antibody" refers to an immunoglobulin (Ig) molecule, which is generally comprised of four polypeptide chains, two heavy (H) chains and two light (L) chains, or a functional fragment, mutant, variant, or derivative thereof, that retains the epitope binding features of an Ig molecule. Such fragment, mutant, variant, or derivative antibody formats are known in the art. In an embodiment of a full-length antibody, each heavy chain is comprised of a heavy chain variable region (VH) and a heavy chain constant region (CH). The heavy chain variable region (domain) is also designated as VDH in this disclosure. The CH is comprised of three domains, CH1, CH2 and CH3. Each light chain is comprised of a light chain variable region (VL) and a light chain constant region (CH). The CL is comprised of a single CL domain. The light chain variable region (domain) is also designated as VDL in this disclosure. The VH and VL can be further subdivided into regions of hypervariability, termed complementarity determining regions (CDRs), interspersed with regions that are more conserved, termed framework regions (FRs). Generally, each VH and VL is composed of three CDRs and four FRs, arranged from amino-terminus to carboxy-terminus in the following order: FR1, CDR1, FR2, CDR2, FR3, CDR3, and FR4. Immunoglobulin molecules can be of any type (e.g., IgG, IgE, IgM, IgD, IgA and IgY), class (e.g., IgG1, IgG2, IgG3, IgG4, IgA1 and IgA2), or subclass.

The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3.

The term "recombinant human antibody", as used herein, is intended to include all human antibodies that are prepared, expressed, created or isolated by recombinant means, such as antibodies expressed using a recombinant expression vector transfected into a host cell, antibodies isolated from a recombinant, combinatorial human antibody library, antibodies isolated from an animal (e.g., a mouse) that is transgenic for human immunoglobulin genes (see e.g., Taylor, L. D., et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

The term "biological function" refers the specific in vitro or in vivo actions of a binding protein. Binding proteins may target several classes of antigens/ligands and achieve desired therapeutic outcomes through multiple mechanisms of action. Binding proteins may target soluble proteins, cell surface antigens, as well as extracellular protein deposits. Binding proteins may agonize, antagonize, or neutralize the activity of their targets. Binding proteins may assist in the clearance of the targets to which they bind, or may result in cytotoxicity when bound to cells. Portions of two or more antibodies may be incorporated into a multivalent format to achieve distinct functions in a single binding protein molecule. The in vitro assays and in vivo models used to assess biological function are known to one skilled in the art (US 20090311253).

Binding proteins may be produced using a variety of host cells or may be produced in vitro, and the relative yield per effort determines the "production efficiency." Factors influencing production efficiency include, but are not limited to, host cell type (prokaryotic or eukaryotic), choice of expression vector, choice of nucleotide sequence, and methods employed. The materials and methods used in binding protein production, as well as the measurement of production efficiency, are known to one skilled in the art. See, e.g., US 20090311253.

The terms "recombinant host cell" or "host cell" refer to a cell into which exogenous DNA has been introduced. Such terms refer not only to the particular subject cell, but to the progeny of such a cell. Because certain modifications may occur in succeeding generations due to either mutation or environmental influences, such progeny may not, in fact, be identical to the parent cell, but are still included within the scope of the term "host cell" as used herein. In an embodiment, host cells include prokaryotic and eukaryotic cells. In an embodiment, eukaryotic cells include protist, fungal, plant and animal cells. In another embodiment, host cells include but are not limited to the prokaryotic cell line *E. Coli*; mammalian cell lines CHO, HEK293, COS, NS0, SP2 and PER.C6; the insect cell line Sf9; and the fungal cell *Saccharomyces cerevisiae*.

The term "variant" means a polypeptide that differs from a given polypeptide in amino acid sequence or in post-translational modification. The difference in amino acid sequence may be caused by the addition (e.g., insertion), deletion, or conservative substitution of amino acids, but that retains the biological activity of the given polypeptide (e.g., a variant TNF-alpha antibody can compete with anti-TNF-alpha antibody for binding to TNF-alpha). A conservative substitution of an amino acid, i.e., replacing an amino acid with a different amino acid of similar properties (e.g., hydrophilicity and degree and distribution of charged regions) is recognized in the art as typically involving a minor change. These minor changes can be identified, in part, by considering the hydropathic index of amino acids, as understood in the art (see, e.g., Kyte et al. (1982) J. Mol. Biol. 157: 105-132). The hydropathic index of an amino acid is based on a consideration of its hydrophobicity and charge. It is known in the art that amino acids of similar hydropathic indexes in a protein can be substituted and the protein still retains protein function. In one aspect, amino acids having hydropathic indexes of ±2 are substituted. The hydrophilicity of amino acids also can be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity (see, e.g., U.S. Pat. No. 4,554,101). Substitution of amino acids having similar hydrophilicity values can result in peptides retaining biological activity, for example immunogenicity, as is understood in the art. In one aspect, substitutions are performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties. The term "variant" also includes polypeptide or fragment thereof that has been differentially processed, such as by proteolysis, phosphorylation, or other post-translational modification, yet retains its biological activity or antigen reactivity, e.g., the ability to bind to TNF-alpha. The term "variant" encompasses fragments of a variant unless otherwise defined. A variant may be 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, or 75% identical to the wild-type sequence.

The difference in post-translational modification may be effected by addition of one or more chemical groups to the amino acids of the modified molecule, or removal of one or more such groups from the molecule. Examples of modification may include but are not limited to, phosphorylation, glysosylation, or MGO modification.

It will be readily apparent to those skilled in the art that other suitable modifications and adaptations of the methods described herein are obvious and may be made using suitable equivalents without departing from the scope of the embodiments disclosed herein. Having now described certain embodiments in detail, the same will be more clearly understood by reference to the following examples, which are included for purposes of illustration only and are not intended to be limiting.

EXAMPLES

Example 1

Material and Methods

Cell Culture

A recombinant Chinese Hamster Ovary (CHO) cell line (Cell Line 1) expressing a humanized monoclonal antibody (Antibody 1) was evaluated in 2 different cultures vessels (shaker flasks and 3 L laboratory-scale bioreactors). The cell line was of CHO DUX-B11 origin based on a DHFR (dihydrofolate reductase) expression system and cultured in a chemically defined basal media, and fed periodically with a chemically-defined feed media (CDFM). The media utilized throughout all of the experiments were chemically-defined, and both animal-component free, and protein-free. Each of the respective media were supplemented as needed with selected bioflavonoids to evaluate for their potential impact on the resulting acidic species profile. In preparation of the cultures, the cell lines were serially expanded through separate seed train inoculums to generate enough cells for inoculation. Process conditions utilized during the cultures were slightly different depending on the culture scale, but similar within each scale to the respective non-bioflavonoid supplemented control conditions. All bioflavonoids utilized were purchased from Sigma-Aldrich (St. Louis, Mo.).

Viable cell density (VCD) and cell viability values were measured through trypan blue exclusion via Cedex automated cell counters (Roche Applied Science, Indianapolis, Ind.), glucose and lactate values were measured with a ABL-805 (Radiometer Medical, Denmark) blood gas analyzer. Offline pH, dissolved oxygen (DO), and $pCO_2$ measurements were performed as needed with an ABL-805 (Radiometer Medical, Denmark) blood gas analyzer. Osmolality was measured as needed on a Multi-Osmette 2430 osmometer (Precision Systems, Natick, Mass.).

Protein a Affinity Chromatography—

Antibody titers were measured from crude cell culture harvests on a Poros A™ (Life Technologies, Carlsbad, Calif.) affinity column using an HPLC system operating with a low pH, step elution gradient with detection at 280 nm. Absolute concentrations were assigned with respect to reference standard calibration curves.

Purified antibodies subjected to additional analytical characterization were purified using MabSelect™ Protein A (GE Healthcare, Piscataway, N.J.) using a low pH, step elution gradient, followed by buffer exchange (when needed) using Corning Lifesciences (Tewksbury, Mass.) Spin Concentrator X UF columns according to the manufacturers' recommended procedures.

Charge Heterogeneity via Weak Cation Exchange Chromatography—

Figure 2:
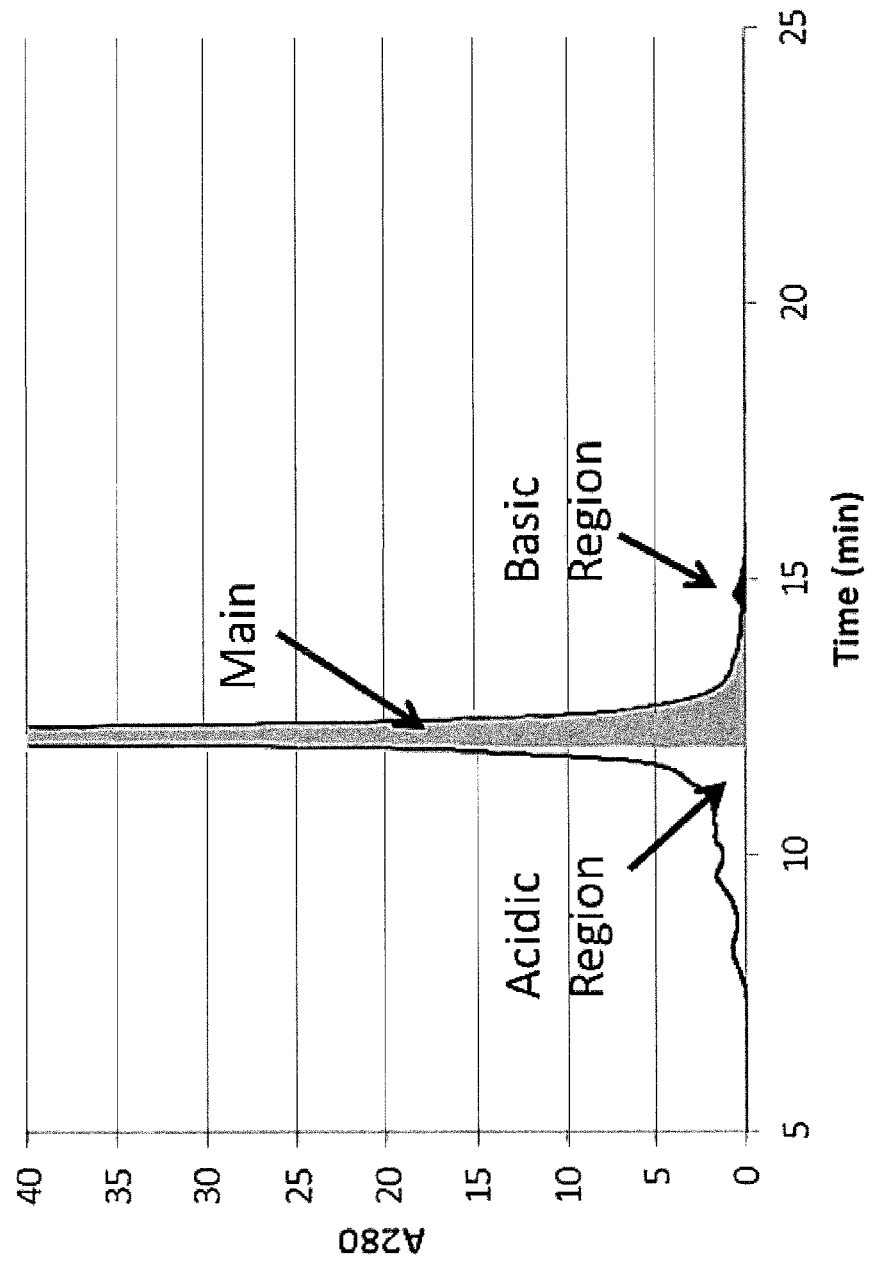
FIG. 2 shows elution profile of the main peak, the acidic species and the basic species of the protein expressed in cell culture.

Samples were analyzed using an HPLC system equipped with a ProPac WCX-10 analytical column (Thermo Scientific, Sunnyvale, Calif.). Approximately 100 μg of sample was loaded in 6% Buffer B (10 mM sodium phosphate, 500 mM NaCl, pH 5.5) and 94% Buffer A (10 mM sodium phosphate, pH 7.5). The column was run at a flow rate of 1.0 mL/min. The protein was eluted from the column by increasing the buffer B composition from 6% to 16% over 20 minutes. The protein peaks were measured using UV absorbance at 280 nm as the peaks eluted from the column. The column was regenerated using 100% buffer B followed be a re-equilibration period using initial condition before the injection of the next sample. Peaks eluting before the main peak were termed "acidic peaks" and peaks eluting after the main peak were called "basic peaks" (FIG. 2).

Size Exclusion Chromatography (SEC)—

Protein A purified antibody samples from Cell Line 1 were diluted when necessary to 0.5-5 mg/mL in 1×PBS, and measured on a TSKgel G3000SW$_{XL}$ column (Tosoh Bioscience, South San Francisco, Calif.) using an isocratic gradient on an HPLC system with detection at 280 nm. High molecular weight (HMW), monomer, and low molecular weight (LMW) species were assigned and subsequently quantitated based on the chromatographic profile.

Flow Cytometry—

At least $10 \times 10^6$ cells were harvested from 3 L bioreactor cultures on Days 6, 8, 12, and 15 after inoculation. Immediately after sampling, the samples were centrifuged and the cell pellet was washed with 1×PBS, and re-suspended in 1 mL of pre-warmed 1×PBS. 2 μL of 2 mM H2-DCF (Life Technologies, Grand Island, N.Y.) in DMSO (Sigma-Aldrich, St. Louis, Mo.) was then added and incubated at 37° C. for 30 minutes and covered from light. The cell suspension was then centrifuged and resuspended in 1×PBS twice to wash the cells and remove residual fluorophore. The cells were then loaded onto a FACSCalibur (Becton Dickinson, Franklin Lakes, N.J.) flow cytometer for the measurement of intracellular ROS at 492-495 nm/517-527 nm excitation/emission.

Example 2

Determining the Impact of EGCG on Product Quality of Antibody 1

In this Example, EGCG was added into the feed (cell culture medium) at the concentration range of 5 mg/L (low), 20 mg/L (mid) and 50 mg/L (high) in a shaker experiment to determine the impact of EGCG on product quality of a humanized monoclonal antibody (Antibody 1). Detailed cell culture conditions are as described in Table 1.

TABLE 1

Cell culture process conditions & bioflavonoid supplementation for Cell line 1

| Culture Vessel | Shaker flasks | 3L lab-scale bioreactors |
|---|---|---|
| Culture Mode | Fedbatch | Fedbatch |
| Initial Culture Temperature (° C.) | 36 | 36 |
| Dissolved Oxygen (%) | N/A[a] | 30-40 |
| pH | N/A[a] | 6.9 |
| Bioflavonoids Evaluated[b] | EGCG Rutin Naringin Genistein | EGCG Rutin |
| Supplement Concentrations (g/L) | 0.005, 0.01, 0.02, 0.05, 0.1, 0.5 0.02, 0.1, 1.0 0.02, 0.1, 1.0 0.01, 0.1, 0.5 | 0.02, 0.05, 0.1, 0.125, 0.25 0.1 |

[a]Cultures run in $CO_2$ incubators at 5% $CO_2$ in air; pH and DO parameters were not controlled, and thus did not have setpoint values.
[b]Supplements added to chemically-defined feed media only.

Figure 3:
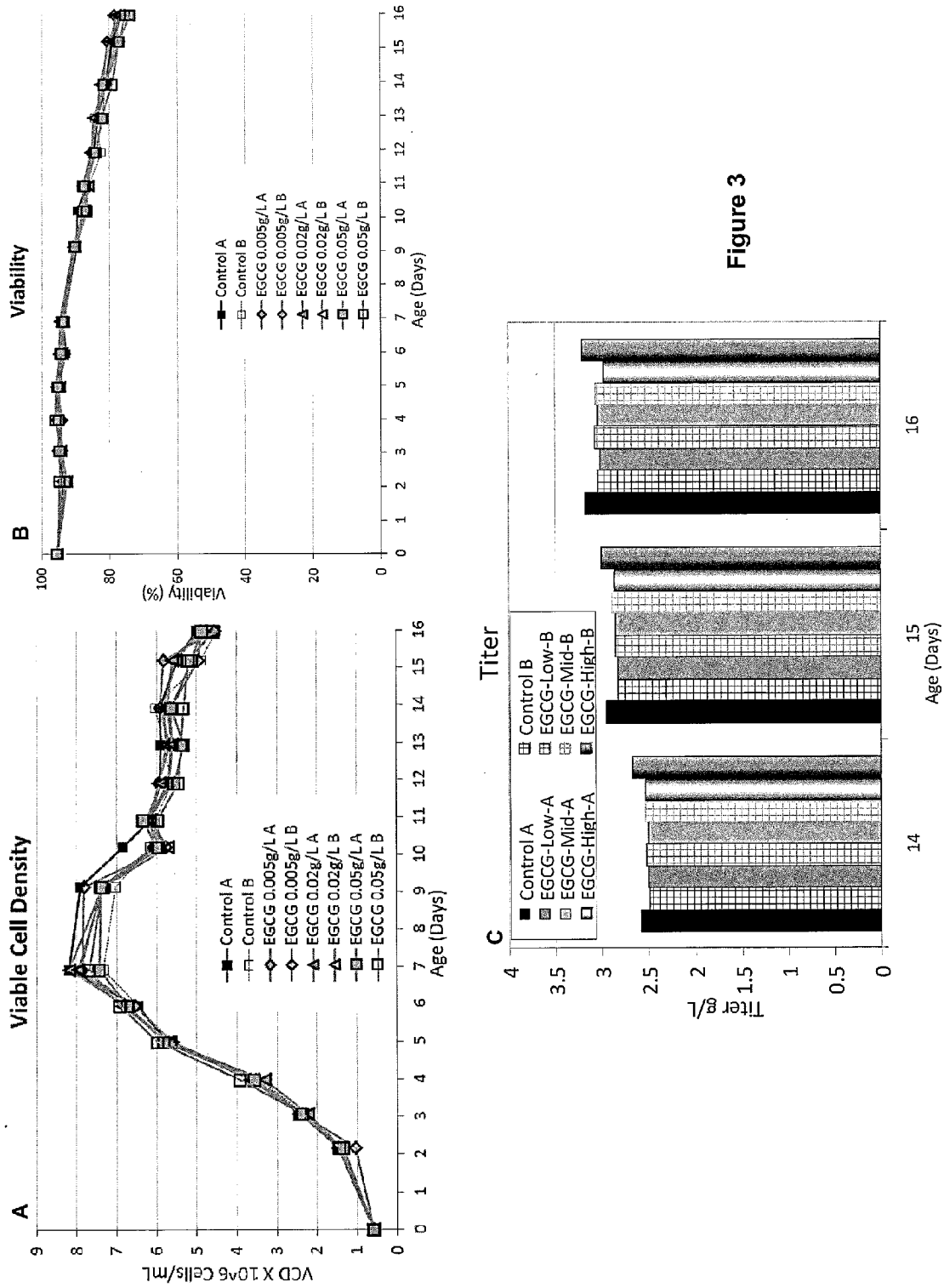
FIG. 3 shows the effect of EGCG supplement on Antibody 1 in shake flask fed-batch culture on a) cell growth b) viability c) titer.

At the tested concentrations (5 mg/L (low), 20 mg/L (mid) and 50 mg/L (high)), EGCG had no impact on cell culture performance, including cell growth (FIG. 3A), viability (FIG. 3B), and titer (FIG. 3C). The growth profile, viability and productivity of the cell culture supplemented with EGCG were very similar to control cultures without the EGCG supplementation.

Figure 4:
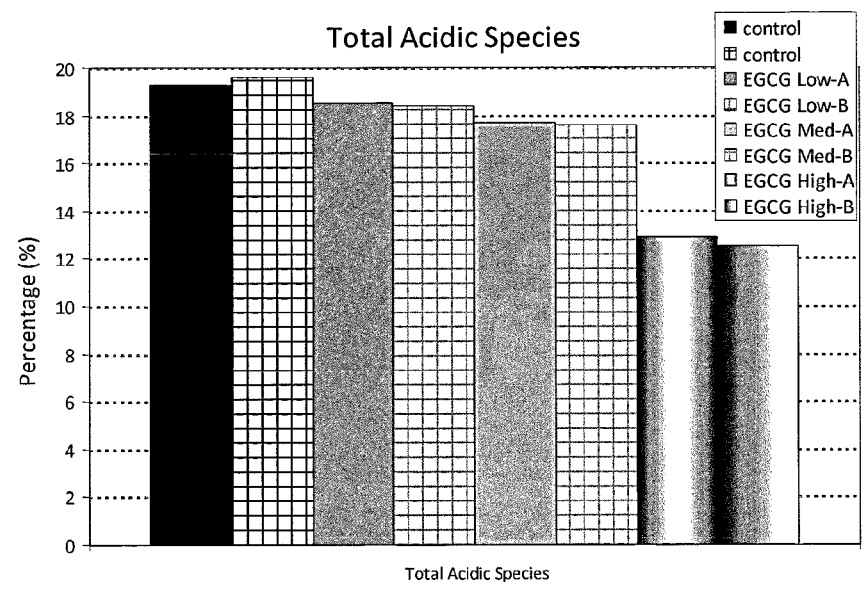
FIG. 4 shows the effect of EGCG supplement on Antibody 1 in shake flask fed-batch culture on a) the percentage of acidic species b) size content.
Figure 4:
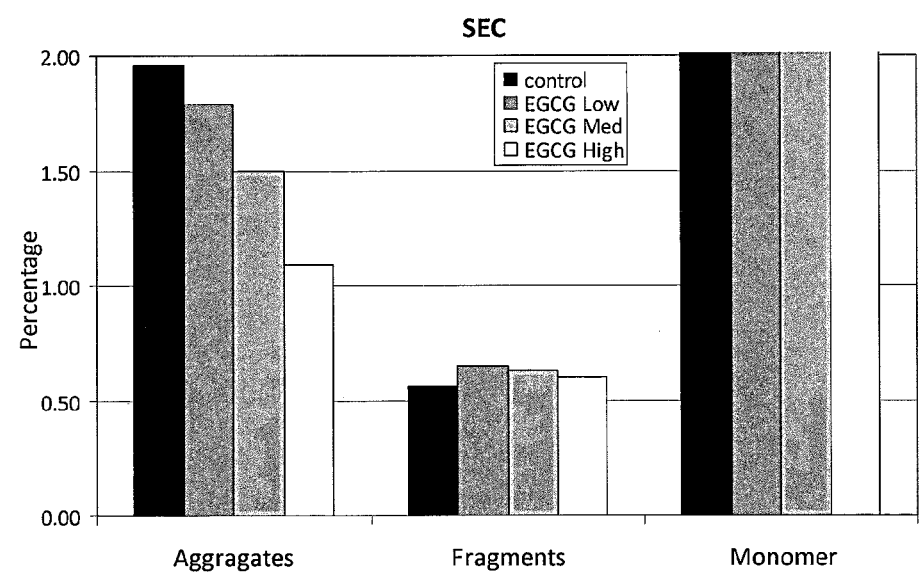

The charge variants content of the cell cultures were also evaluated. EGCG supplement reduced the total acidic species in a dose-dependent manner. The total acidic species content decreased as the concentration of EGCG increases. At the concentrations of 5 mg/L, 20 mg/L and 50 mg/L, EGCG reduced the total acidic species content by 1%, 2% and 7% in absolute value, and 5%, 10% and 35% in relative value, respectively (FIG. 4A). Size Exclusion Chromatography (SEC) results showed that EGCG supplement reduced the total aggregate content in a dose-dependent manner. The total aggregation level decreased as the concentration of EGCG increased. At the concentrations of 5 mg/L, 20 mg/L and 50 mg/L, EGCG reduced the aggregation content by 9%, 23% and 44% in relative value, respectively (FIG. 4B). It is to be noted that the total aggregation level of Antibody 1 was low (2%) even without EGCG supplement. The sensitivity of the SEC method and the dose-dependent manner on the aggregation level by EGCG suggests that EGCG supplement reduces aggregation.

Figure 5:
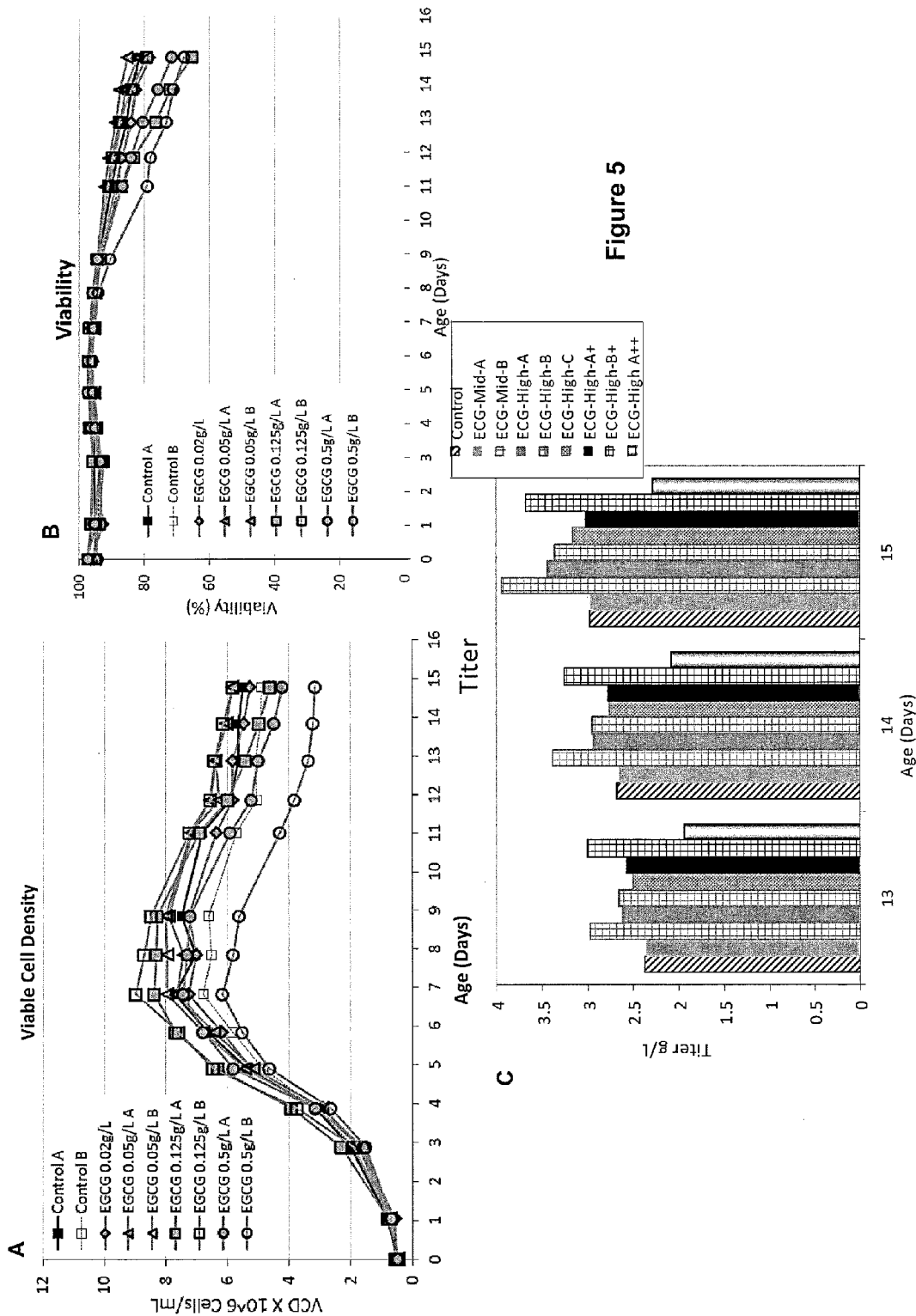
FIG. 5 shows the effect of EGCG supplement on Antibody 1 in bioreactor fed-batch culture on a) cell growth b) viability c) titer.

In the next experiment, lab-scale bioreactors were used to (1) confirm the shaker experiment results and (2) to determine whether higher concentration range of EGCG is suitable for supplementing into cell culture. EGCG was added to the feed of the batch culture at the concentrations of 20 mg/L (mid), 50 mg/L (high) and 125 mg/L (high+) and 250 mg/L (high++) in this reactor experiment. EGCG supplemented to 1.5×JCL5 feed media at the concentrations of 20 mg/L, 50 mg/L and 125 had no impact on cell culture performance, including cell growth (FIG. 5A), viability (FIG. 5B) and titer (FIG. 5C). At the concentration of 250 mg/L, EGCG caused a reduction in early cell culture viability and titer reduction.

Figure 6:
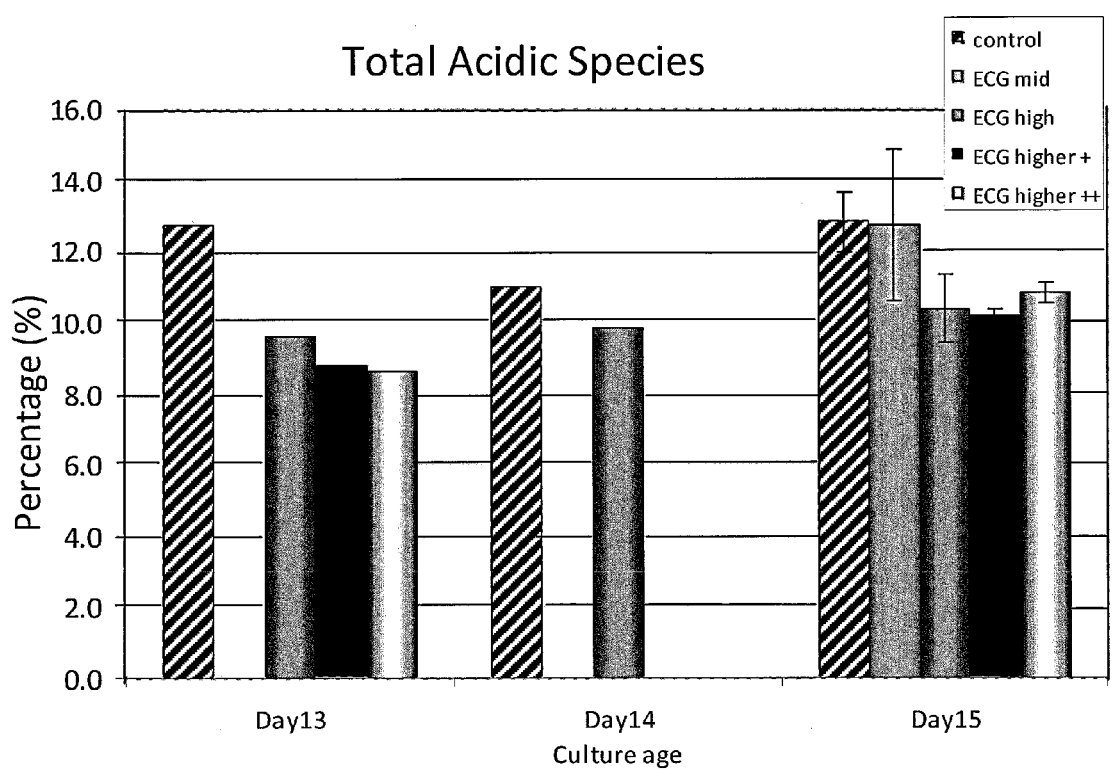
FIG. 6 shows the effect of EGCG supplement on Antibody 1 in bioreactor fed-batch culture on the percentage of acidic species.

The effect of higher concentration of EGCG on charge variants content was also determined. At the concentrations of 50 mg/L (high) and 125 mg/L (high+) and 250 mg/L (high++), EGCG reduced the total acidic species content at the level of at least 2% in absolute value and 16% in relative value (FIG. 6).

Figure 7:
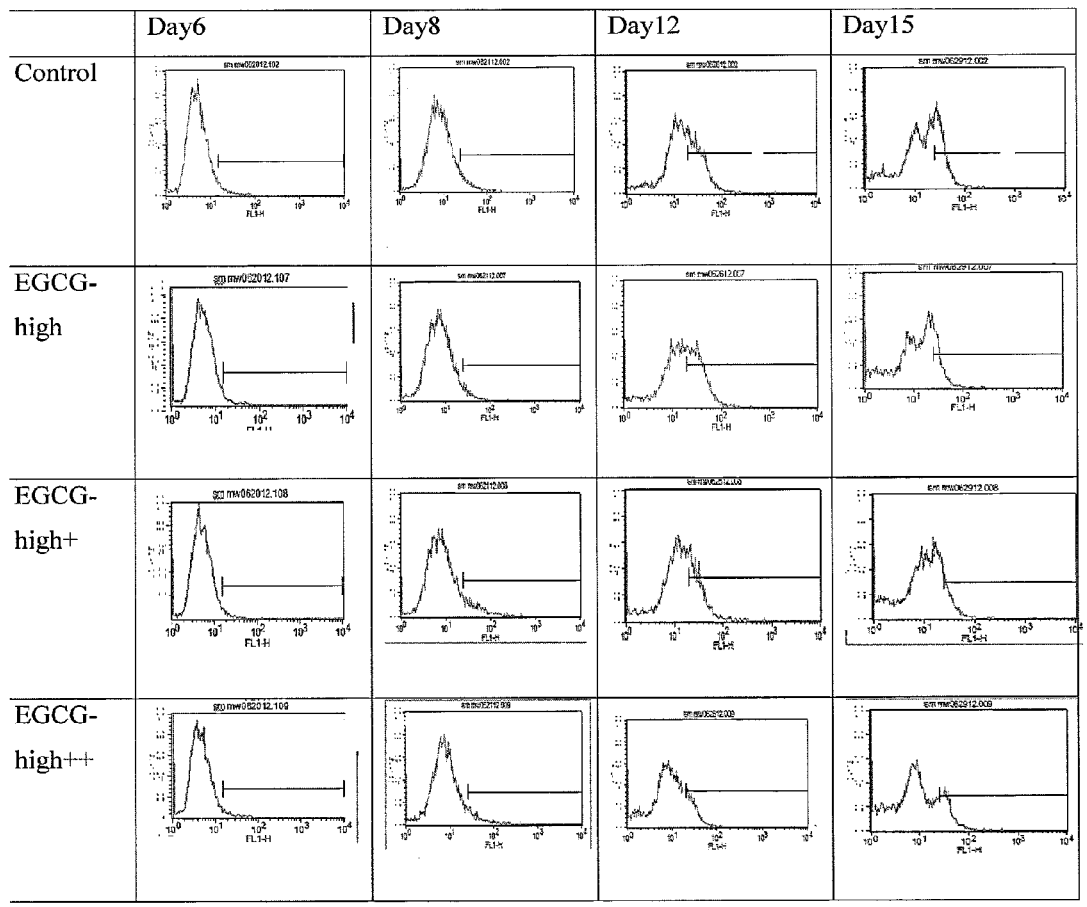
FIG. 7 shows the effect of EGCG supplement on Antibody 1 in bioreactor fed-batch culture on intracellular ROS (reactive oxygen species) level.

Flow cytometry data showed that as the cell culture ages, the ROS (reactive oxidative species) were accumulated intracellularly in a time-dependent manner (FIG. 7). EGCG reduced the intracellular ROS level in a dose-dependent fashion. The underlying mechanisms for EGCG mediated reduction of acidic species may be through EGCG's capability of reducing the intracellular ROS level. This dataset shed lights on the potential mechanism of flavonoid family's impact on acidic species reduction and aggregation reduction in the cell culture process of bio-therapeutics production. It is likely that the increased ROS level might have contributed, at least in part, to the increase in acidic species, especially toward the end of the culture. The role of EGCG in mitigating the intracellular ROS stress may explain why EGCG supplementation might help reduce acidic species in the antibodies.

Example 3

Evaluation of Alternative Bioflavonoids for the Impact on Product Quality of Antibody 1-Shake Flask Cultures In the Examples above, the bioflavonoid EGCG has been shown to be effective towards reduction of acidic species variants on Antibody 1. However, it was not clear whether or not additional bioflavonoids would also have the same effects. To evaluate the impact of alternative bioflavonoids, fed-batch shake flask cultures were initiated with CDFM supplemented with 3 different concentrations of genistein, rutin, and naringin, in addition to EGCG. Cell growth, viability, as well as titers and acidic species variants were measured. The results are shown in FIG. 8 and FIG. 9.

As evidenced by the cell growth curves, when EGCG concentrations were above 0.1 g/L in the CDFM, cell growth was adversely impacted. Under those EGCG concentrations, the culture was only capable of reaching 8 days, before the associated cell viability became too low for the culture to proceed. At 0.1 g/L EGCG, the cell growth was also significantly lower than that of the control culture. However, at 0.1 g/L EGCG the cell viability remained comparable to the control, and the cultures were able to proceed until Day 12.

Figure 8:
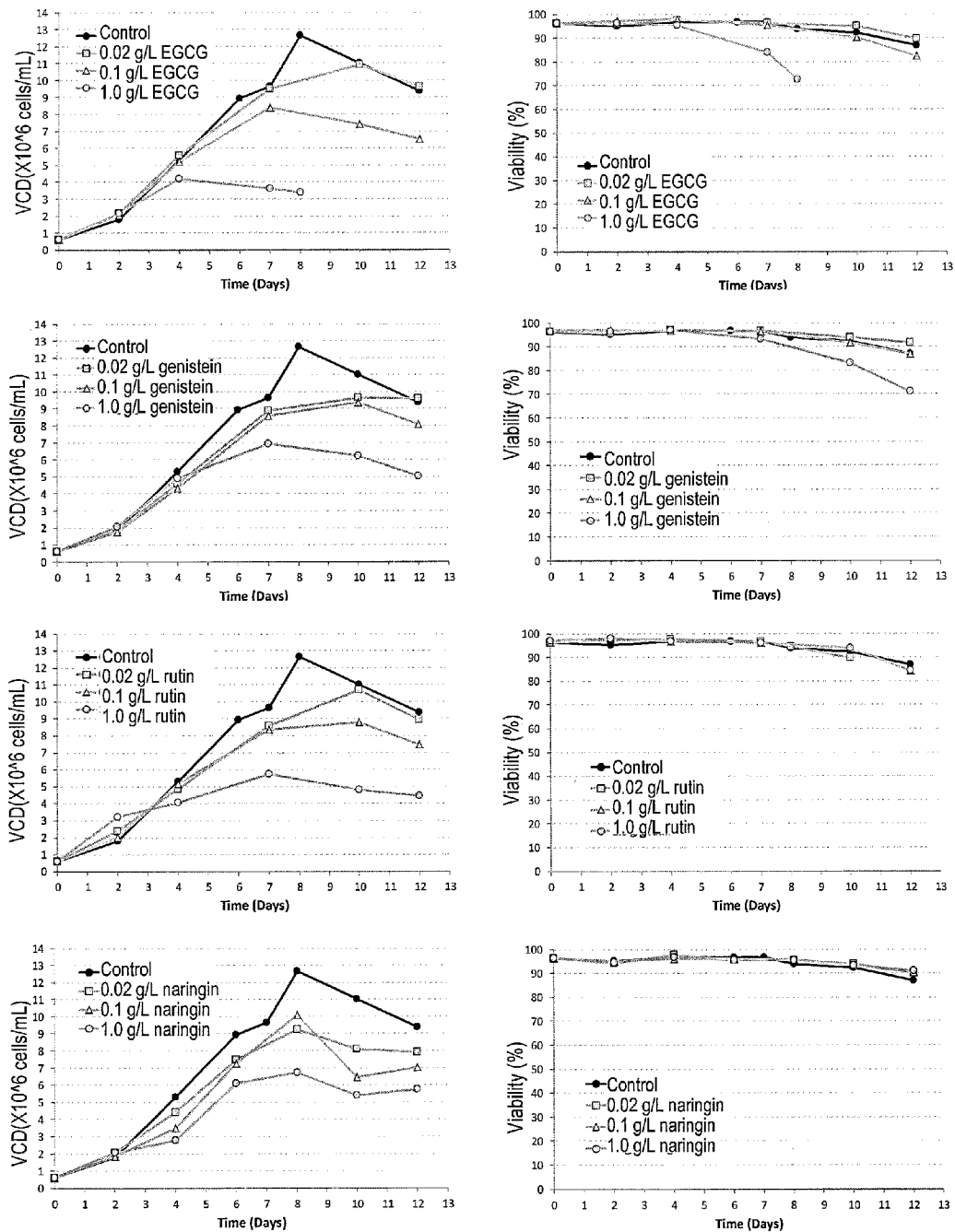
FIG. 8 shows cell growth and viability profiles of Cell Line 1 cultured with and without various bioflavonoids.

In the genistein, rutin, and naringin supplemented cell culture conditions, all 3 bioflavonoids resulted in cell growth profiles that were lower than the unsupplemented control condition (FIG. 8). Common to all 3 bioflavonoids was a concentration-dependent decrease in cell growth as the supplement concentrations were increase to 0.5 g/L (genistein), or 1 g/L (rutin and naringin). With the exception of 0.5 g/L genistein, every concentration of the alternative bioflavonoids evaluated was capable of supporting a cell viability that was similar to the control, and the cultures were able to proceed until Day 12.

Figure 9:
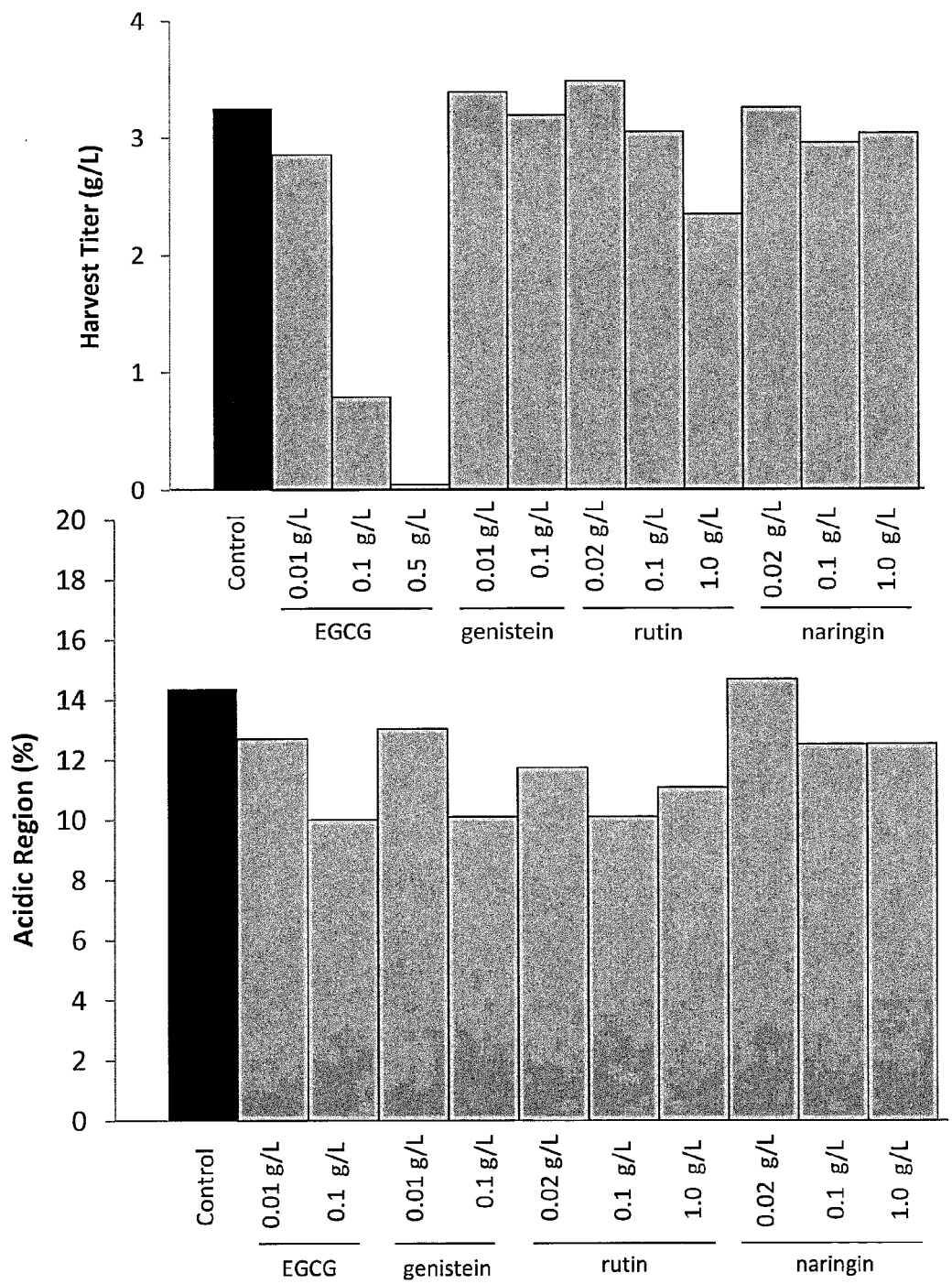
FIG. 9 shows harvest titer, and relative acidic species variants at harvest for Cell Line 1 cultured with and without various bioflavonoids.

FIG. 9 shows the harvest titers and acidic species variants for the cultures described above which were able to reach completion on Day 12 with a harvest viability greater than 80%. Among these cultures, it is readily apparent that those cultures which received the higher levels of EGCG had a decreased titer. Among the alternative bioflavonoids, with the exception of 1.0 g/L rutin, all of the cultures, regardless of the bioflavonoid concentration evaluated, were capable of producing comparable amounts of Antibody 1 as compared to the unsupplemented control. These results indicate that although the evaluated bioflavonoids may decrease cell growth at higher concentrations, they support a cell viability, and harvest titer levels comparable to those of the control cultures.

The levels of acidic species variants on Antibody 1 from the various cultures were measured and compared. In majority of the cases, significant drop in acidic species variants (1-5%) was observed in those cultures treated with the supplements. This decline in acidic species suggests that higher levels of EGCG, genistein, rutin, and naringin in the cultures might have been responsible for the decline in acidic species. As the concentration of these compounds increased in the cell culture feed media, the acidic region (AR) decreased proportionally.

In summary, these results suggest that the tested bioflavonoids, including EGCG, are capable of significantly reducing the overall levels of acidic species on recombinant proteins. The type of supplementation and the concentrations of the supplement may be determined based on specific circumstances to ensure that the resulting drop in acidic species is not achieved at the expense of the harvest titer.

Example 4

Figure 10:
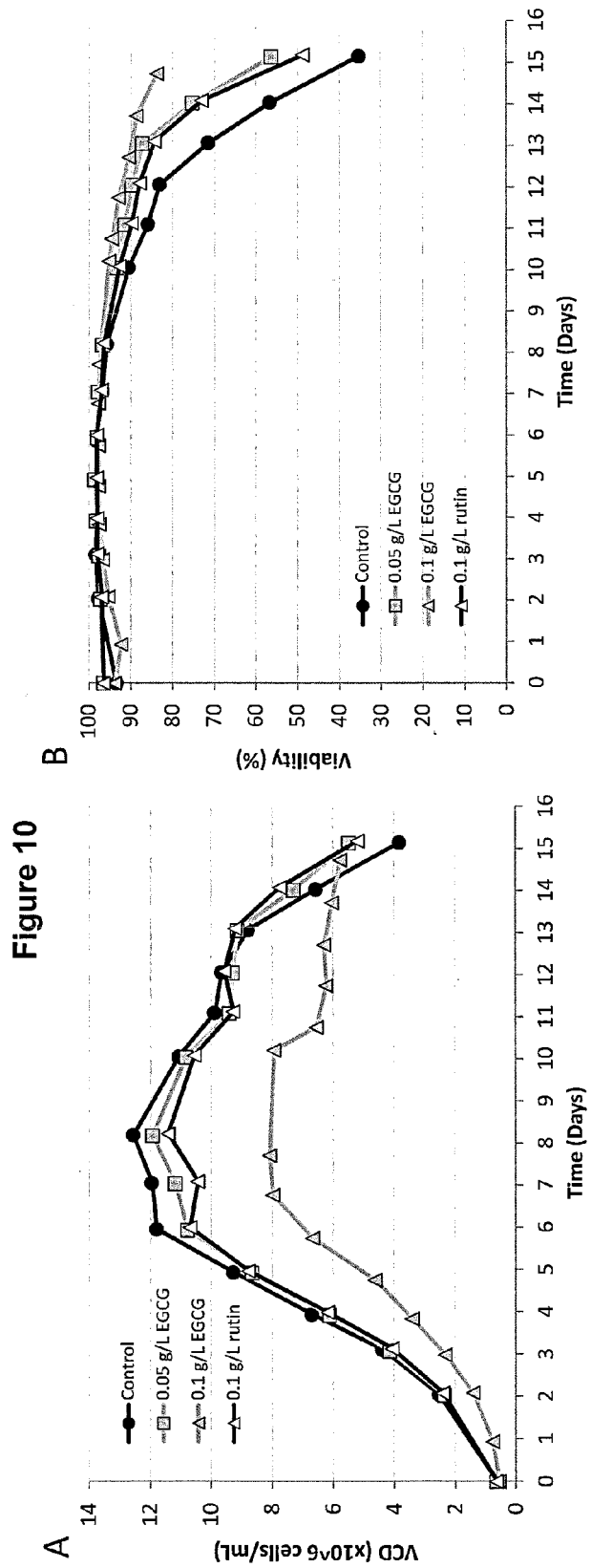
FIG. 10 shows (A) Cell growth, (B) viability, (C) harvest titer, (D) harvest acidic species levels (E) representative WCX-10 chromatogram of Cell Line 1 cultured in various bioflavonoids in lab-scale bioreactor cultures.
Figure 10:
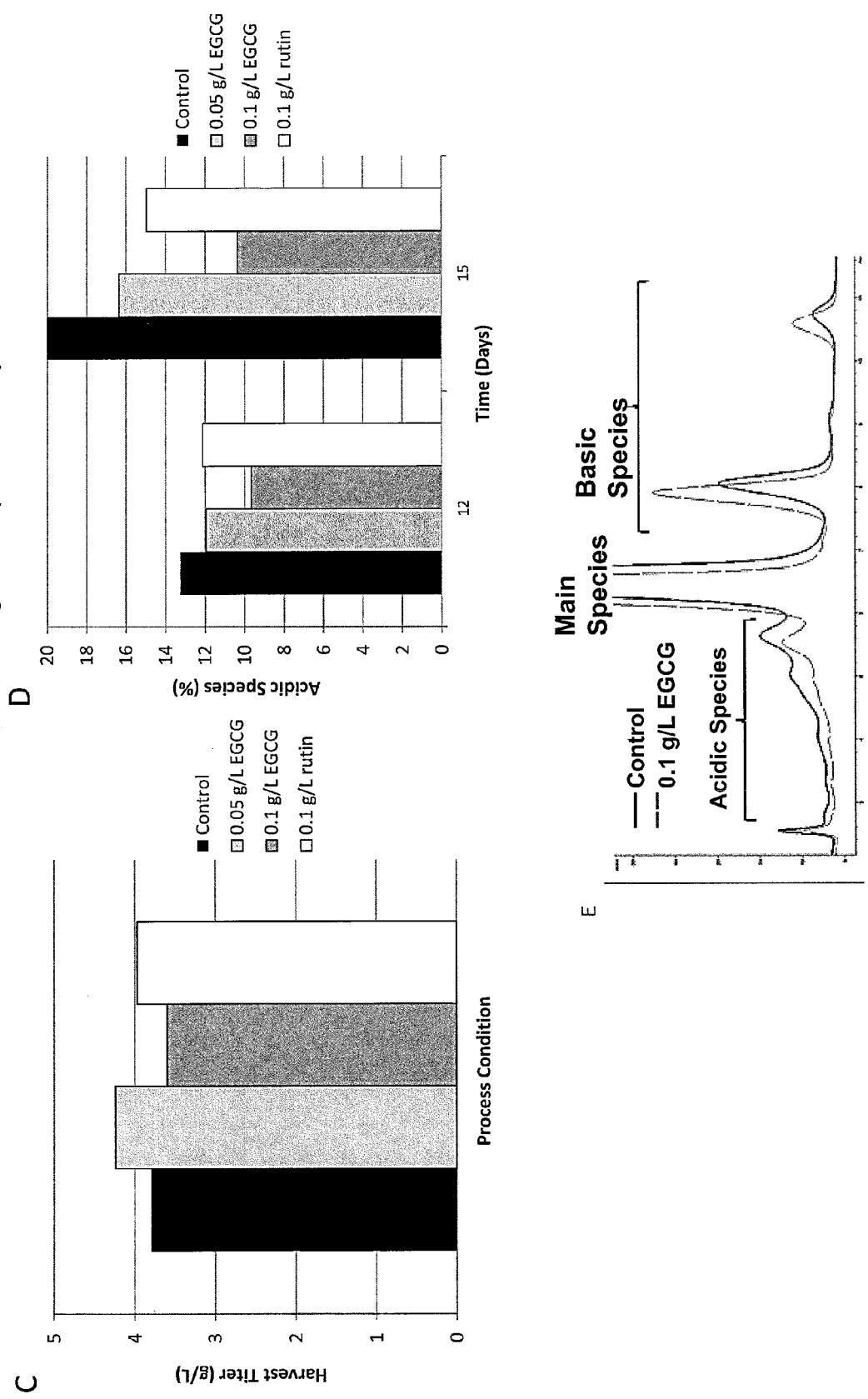

Evaluation of Alternative Bioflavonoids for the Impact on Product Quality of Antibody 1 in 3 L Bioreactor Cultures Cell Line 1 was evaluated in larger-scale feed batch cultures with the feed media supplemented with various bioflavonoids. The resulting impact on cell culture process performance is shown in FIG. 10. Those cultures containing CDFM supplemented with 0.05 g/L EGCG and 0.1 g/L rutin exhibited cell growth with peak viable cell densities reaching approximately $12 \times 10^6$ cells/mL on Day 8 of the cultures. These growth parameters were comparable to those of the control cultures with no bioflavonoid supplementation. Cell viabilities were above 90% for the majority of the culture duration, with the bioflavonoid supplemented cultures demonstrating a higher cell viability throughout the terminal stages of the cultures as compared to the control cultures (FIG. 10B). By contrast, cell growth performance was slightly different for the 0.1 g/L EGCG supplemented condition. Similar to the results from the shake flask studies, at 0.1 g/L EGCG in the CDFM, the cell growth profile was lower than the unsupplemented control culture. However, the cell viability remained high at 0.1 g/L EGCG. All cultures were successfully harvested on Day 15 post-inoculation. The harvest titers measured from the evaluated cultures were similar. Note that the 0.05 g/L EGCG and 0.1 g/L rutin conditions outperformed the control condition by a nominal amount.

The acidic species profile for the 0.05 g/L and 0.1 g/L EGCG CDFM supplemented cultures, as well as the 0.1 g/L rutin supplemented culture all demonstrated lower levels compared to the unsupplemented CDFM control (FIG. 10D). This decrease was observed as early as Day 12 of the cultures, and became even more pronounced by the time the cultures were harvested on Day 15. Among the evaluated conditions, 0.1 g/L EGCG performed the best with an outstanding 10% drop in absolute acidic species percentage points. The 0.1 g/L rutin CDFM supplemented culture performed well with a 5% drop in acidic species variants, followed by the 0.05 g/L EGCG CDFM supplemented culture, which demonstrated a 4% drop (FIG. 10D). Similar to the shake flask cultures tests described above, there was a concentration-dependent drop in acidic species as the bioflavonoid concentrations increased in the CDFM. Note an increase of total acidic species in the unsupplemented control culture that appeared between Days 12 and 15. When bioflavonoid was included in the culture, this late stage increase in acidic species was significantly mitigated. These results are consistent with the aforementioned flow cytometry results which indicated that ROS levels increase significantly during this same time period. It is possible that bioflavonoids affect the overall ROS levels, and prevent their late-stage increase in the culture. By depressing ROS levels as the cells are aging and dying in late-stage cultures, bioflavonoids may directly affect the subsequent levels of acidic species variants.

Example 5

Assessing the Impact of Bioflavonois on Product Quality of Antibody 1, Antibody 2, DVD1 and DVD2 Expressed in CHO Cell Lines Four different recombinant Chinese Hamster Ovary (CHO) cell lines expressing four different recombinant glycoproteins were evaluated in either shaker flask culture, or 3 L laboratory scale bioreactors. Cell Line 1 was genetically engineered to express Antibody 1, Cell Line 2 was genetically engineered to express Antibody 2, Cell Line 3 was genetically engineered to express dual variable domain immunoglobulin 1 (DVD1) and Cell Line 4 was genetically engineered to express dual variable domain immunoglobulin 2 (DVD2).

DVD1 and DVD2 were immunoglobulins with two variable domains as documented previously. See Wu et al. (2007). Antibody 1 and Antibody 2 were both IgG1 glycoproteins. All four cell lines were of CHO DUX-B11 origin based on a dhfr (dihydrofolate reductase) expression system and cultured in chemically defined basal medias (CDBM), and fed periodically with chemically-defined feed media (CDFM). All media utilized throughout all of the experiments were chemically-defined, free of animal-component, and protein-free. Each of the respective feed medias from each experiment were supplemented as needed with selected bioflavonoids to evaluate their potential impact on the resulting acidic species profile.

In preparation of the cultures, the cell lines were serially expanded through separate seed train inoculums to generate enough cells for inoculation. Process conditions utilized during the cultures were slightly different depending on the culture scale, but similar within each scale to the respective non-bioflavonoid supplemented control conditions (Table 2). All bioflavonoids utilized were purchased from Sigma-Aldrich (St. Louis, Mo.).

TABLE 2

Summary of cell culture process conditions & bioflavonoid supplementation

|  | Cell Line 1 | Cell Line 1 | Cell Line 2 | Cell Line 2 | Cell Line 3 | Cell Line 4 |
|---|---|---|---|---|---|---|
| Culture Vessel | 250 mL shaker flasks | 3 L lab-scale bioreactors | 250 mL shaker flasks | 3 L lab-scale bioreactors | 250 mL shaker flasks | 250 mL shaker flasks |
| Culture Mode | Fedbatch | Fedbatch | Fedbatch | Fedbatch | Fedbatch | Fedbatch |
| Initial Culture Temperature (° C.) | 36 | 36 | 36 | 36 | 36 | 35 |
| Dissolved Oxygen Setpoint (%) | N/A[a] | 30-40 | 40 | 40 | N/A[a] | N/A[a] |
| pH Setpoint | N/A[a] | 6.9 | N/A[a] | 6.9 | N/A[a] | N/A[a] |
| Bioflavonoids Evaluated[b] | EGCG and Rutin, separately | EGCG and Rutin, separately | EGCG | EGCG | EGCG | Rutin |
| Supplement Concentrations (g/L) | EGCG: 0, 0.005, 0.02, 0.05; Rutin: 0, 0.01, 0.05, 0.1, 1.0 | EGCG: 0, 0.02, 0.05, 0.1, 0.125, 0.5; Rutin: 0, 0.1 | EGCG: 0, 0.05, 0.1 | EGCG: 0, 0.05, 0.1 | EGCG: 0, 0.02, 0.05, 0.1, 0.2 | Rutin: 0, 0.01, 0.05, 0.1, 1.0 |

[a]Cultures run in $CO_2$ incubators at 5% $CO_2$ in air; pH and DO (Dissolved oxygen) parameters were not controlled, and thus did not have setpoint values.
[b]Bioflavonoids added to chemically-defined feed media only.

Viable cell density (VCD) and cell viability values were measured through trypan blue exclusion via Cedex automated cell counters (Roche Applied Science, Indianapolis, Ind.), glucose and lactate values were measured with a ABL-805 (Radiometer Medical, Denmark) blood gas analyzer. Offline pH, dissolved oxygen (DO), and $pCO_2$ (Dissolved carbon dioxide) measurements were performed as needed with an ABL-805 (Radiometer Medical, Denmark) blood gas analyzer. Osmolality was measured as needed on a Multi-Osmette 2430 osmometer (Precision Systems, Natick, Mass.).

Protein A Affinity Chromatography-Antibody titers were measured from crude cell culture harvests on a Poros ATM (Life Technologies, Carlsbad, Calif.) affinity column using an HPLC system operating with a low pH, step elution gradient with detection at 280 nm. Absolute concentrations were assigned with respect to reference standard calibration curves.

Purified antibodies subjected to additional analytical characterization were purified using MabSelect™ Protein A (GE Healthcare, Piscataway, N.J.) using a low pH, step elution gradient, followed by buffer exchange (when needed) using Corning Lifesciences (Tewksbury, Mass.) Spin Concentrator X UF columns, or equivalent, according to the manufacturers' recommended procedures.

Charge Heterogeneity via Weak Cation Exchange Chromatography-Samples were analyzed using an HPLC system equipped with a ProPac WCX-10 analytical column (Thermo Scientific, Sunnyvale, Calif.). Approximately 100 μg of sample was loaded in 6% Buffer B (10 mM sodium phosphate, 500 mM NaCl, pH 5.5) and 94% Buffer A (10 mM sodium phosphate, pH 7.5). The column was run at a flow rate of 1.0 mL/min. The protein was eluted from the column by increasing the buffer B composition from 6% to 16% over 20 minutes. The protein peaks were measured using UV absorbance at 280 nm as the peaks eluted from the column. The column was regenerated using 100% buffer B followed be a re-equilibration period using initial condition before the injection of the next sample. Peaks eluting before the main peak were termed 'acidic peaks' and peaks eluting after the main peak were called 'basic peaks' (FIG. 2).

Size Exclusion Chromatography-Protein A purified antibody samples from Cell Line 1 were diluted when necessary to 0.5-5 mg/mL in 1×PBS, and measured on a TSKgel G3000SW$_{XL}$ column (Tosoh Bioscience, South San Francisco, Calif.) using an isocratic gradient on an HPLC system with detection at 280 nm. High molecular weight (HMW), monomer, and low molecular weight (LMW) species were assigned and subsequently quantitated based on the chromatographic profile.

Statistics-Experimental results are expressed as mean±1 SD for those results generated from at least 3 independent cultures. Experimental results are expressed as the mean value for those results generated from less than 3 independent cultures. Results were evaluated for statistical significance (when needed) through 2-sided t-tests, with a requirement of $p<0.05$ relative to the unsupplemented control conditions.

Results for Antibody 1 (Cell Line 1) are as described above in Examples 2-4.

To further evaluate the impact of EGCG on acidic region variants, Antibody 2 and dual variable domain immunoglobulin 1 (DVD1) were examined. Antibody 2 was evaluated in a set of shaker and lab-scale bioreactor experiments with two feed amounts (100% and 50%) as unsupplemented control conditions. EGCG was added at the concentrations of 0.05 g/L and 0.1 g/L into the 100% feed and equivalent of those concentrations in the 50% feed (to have the same EGCG concentration in the cell culture) in a shaker experiment (See Table 2).

Figure 11:
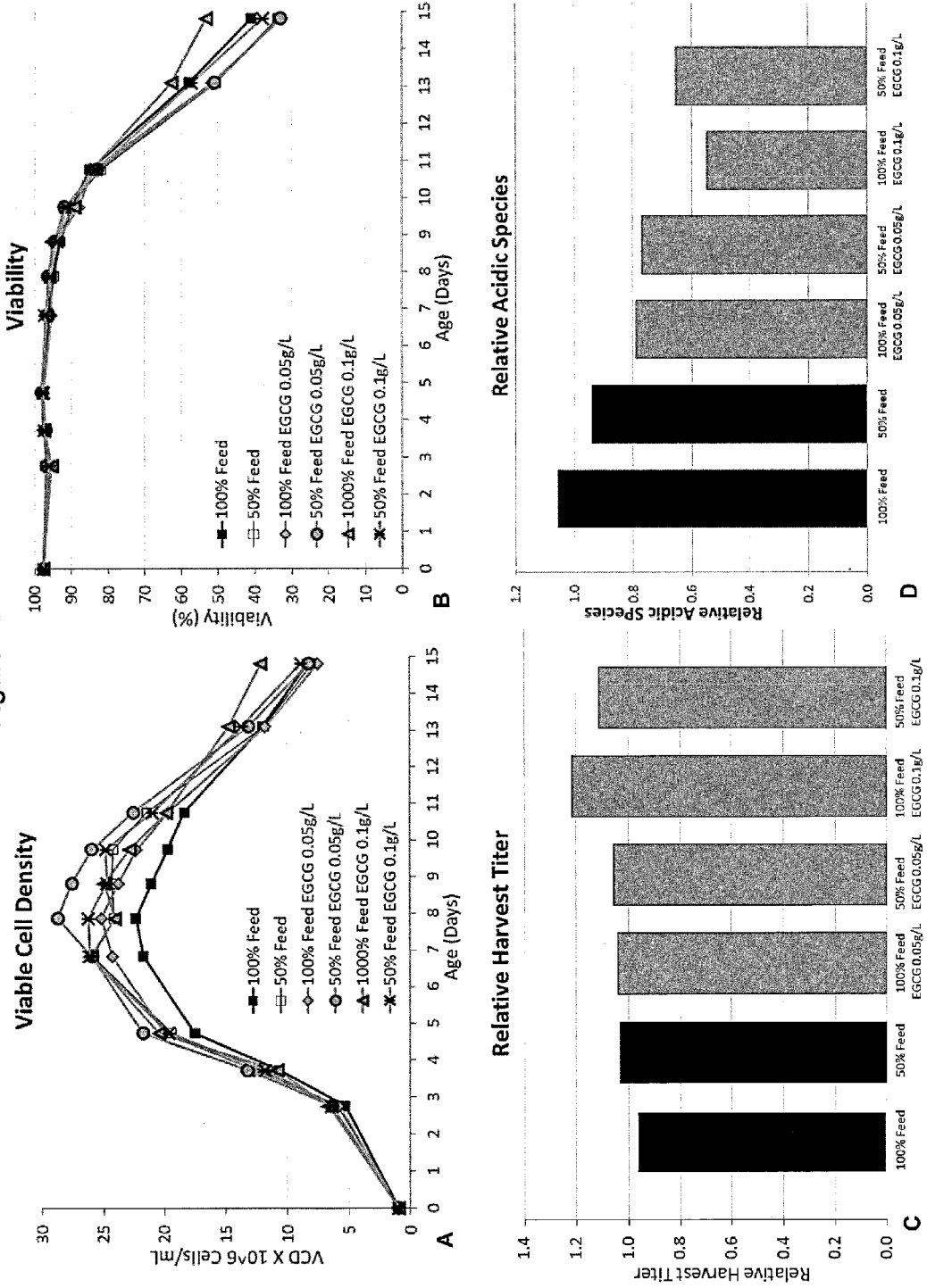
FIG. 11 shows cell culture performance of Cell Line 2 in shake flask culture with EGCG supplemented media. A: Viable cell density. B: Cell viability. C: Relative harvest titer compared to unsupplemented control average. D: Relative acidic species compared to unsupplemented control average.

At the studied concentrations (0.05 g/L and 0.1 g/L), EGCG had no negative impact on cell culture performance, including cell growth (FIG. 11A), viability (FIG. 11B), and titer (FIG. 11C). The EGCG supplemented cultures performed very similarly to control cultures in regards of growth profile, viability with better productivity. At the concentration of 0.1 g/L into the 100% feed and the equivalent concentration in 50% feed, EGCG supplement achieved 1.22 and 1.11 fold of the average titer of the unsupplemented control conditions respectively. Upon measurement of the acidic species variants, EGCG supplement reduced the total acidic species in a dose-dependent manner. The total acidic species content reduces as the concentration of EGCG increases. At the concentrations of 0.05 g/L and 0.1 g/L, respectively, EGCG reduced the total acidic species content 21%-45% relatively compared to the unsupplemented control (FIG. 11D).

Figure 12:
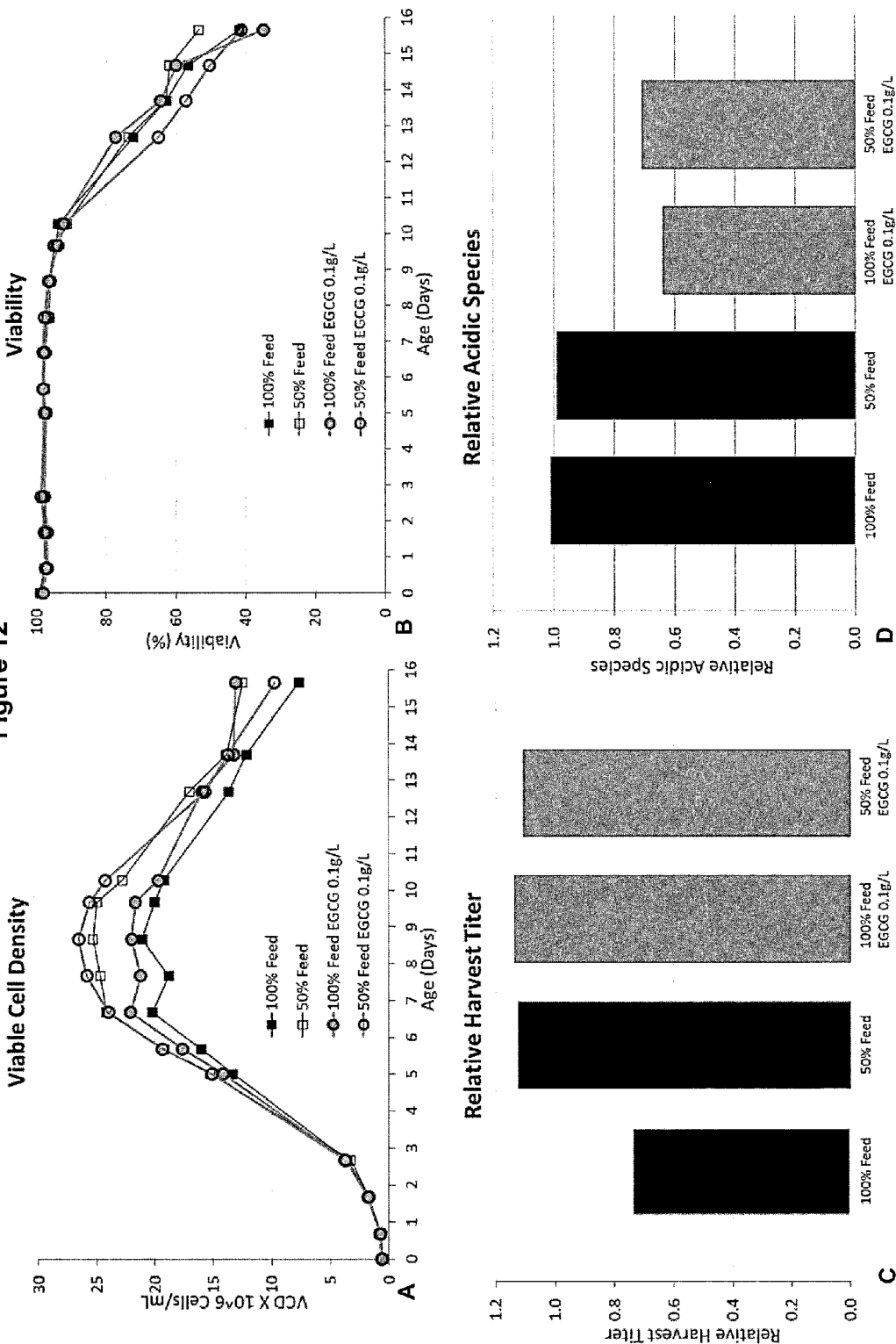
FIG. 12 shows cell culture performance of Cell Line 2 in laboratory-scale bioreactor cultures with EGCG supplemented media. A: Viable cell density. B: Cell viability. C: Relative harvest titer compared to unsupplemented control average. D: Relative acidic species compared to unsupplemented control average.

Lab-scale bioreactors were used to confirm the shaker experiment results seen with Antibody 2. EGCG was added to the feed of the batch culture at the concentrations of 0.1 g/L into the 100% feed and the equivalent concentration into the 50% feed (See Table 2). Overall the cultures with 50% feed reached higher peak VCD compared to the cultures with 100% feed, which is consistent to previous observation with this cell line. EGCG supplemented to the feed media had negligible impact on cell culture performance, including cell growth (FIG. 12A), viability (FIG. 12B) and titer (FIG. 12C). The low titer of 100% feed unsupplemented control condition is possibly an assay measurement excursion, given (1) the other three conditions shared comparable titer (2) the 100% feed supplemented with 0.1 g/L EGCG showed similar growth profile with 100% feed unsupplemented control. Nevertheless, at the concentrations of 0.1 g/L, EGCG reduced the total acidic variants content 29%-36% relatively compared to the unsupplemented control (FIG. 12D).

Figure 13:
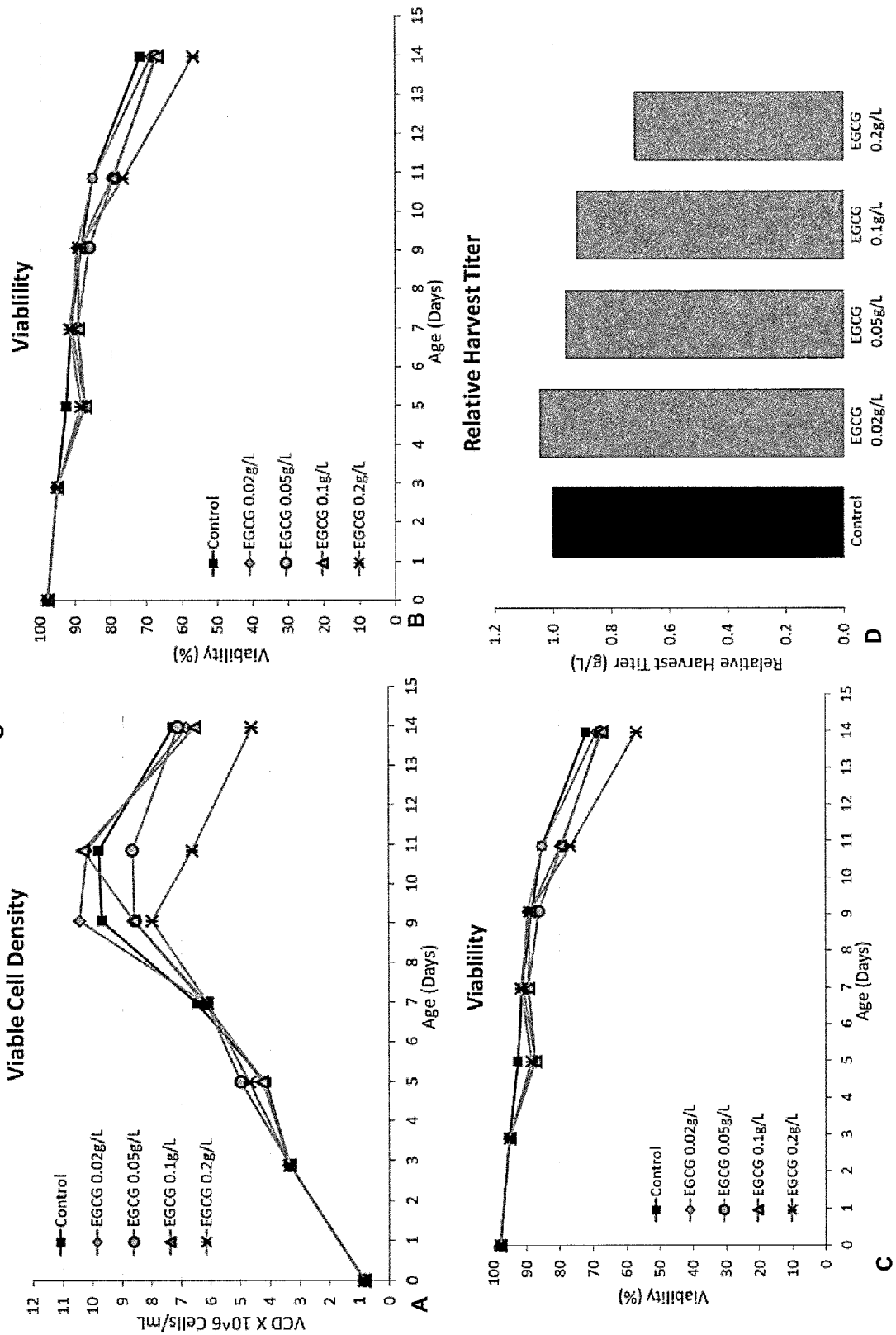
FIG. 13 shows cell culture performance of Cell Line 3 in shake flask culture with EGCG supplemented media. A: Viable cell density. B: Cell viability. C: Relative harvest titer compared to unsupplemented control. D: Relative acidic species compared to unsupplemented control.

To assess the impact of EGCG on acidic region variants on recombinant proteins, dual variable domain immunoglobulin 1 (DVD1) was examined. EGCG was added at the concentrations of 0.02 g/L, 0.05 g/L, 0.1 g/L and 0.2 g/L into the feed in a shaker experiment (See Table 2). At the studied concentrations of 0.02 g/L, 0.05 g/L and 0.1 g/L, the EGCG supplemented cultures performed very similarly to control cultures in regards of growth profile, viability and productivity (FIGS. 13A, 13B and 13C). At the concentration of 0.2 g/L, EGCG led to 15% viability decrease and 28% productivity loss compared to control condition. Upon measurement of the acidic species variants, EGCG supplement reduced the total acidic species in a dose-dependent manner. At the concentrations of 0.02 g/L, 0.05 g/L, 0.1 g/L and 0.2 g/L respectively, EGCG reduced the total acidic species content 5%, 10%, 17% and 22% relatively compared to the unsupplemented control (FIG. 13D).

Figure 14:
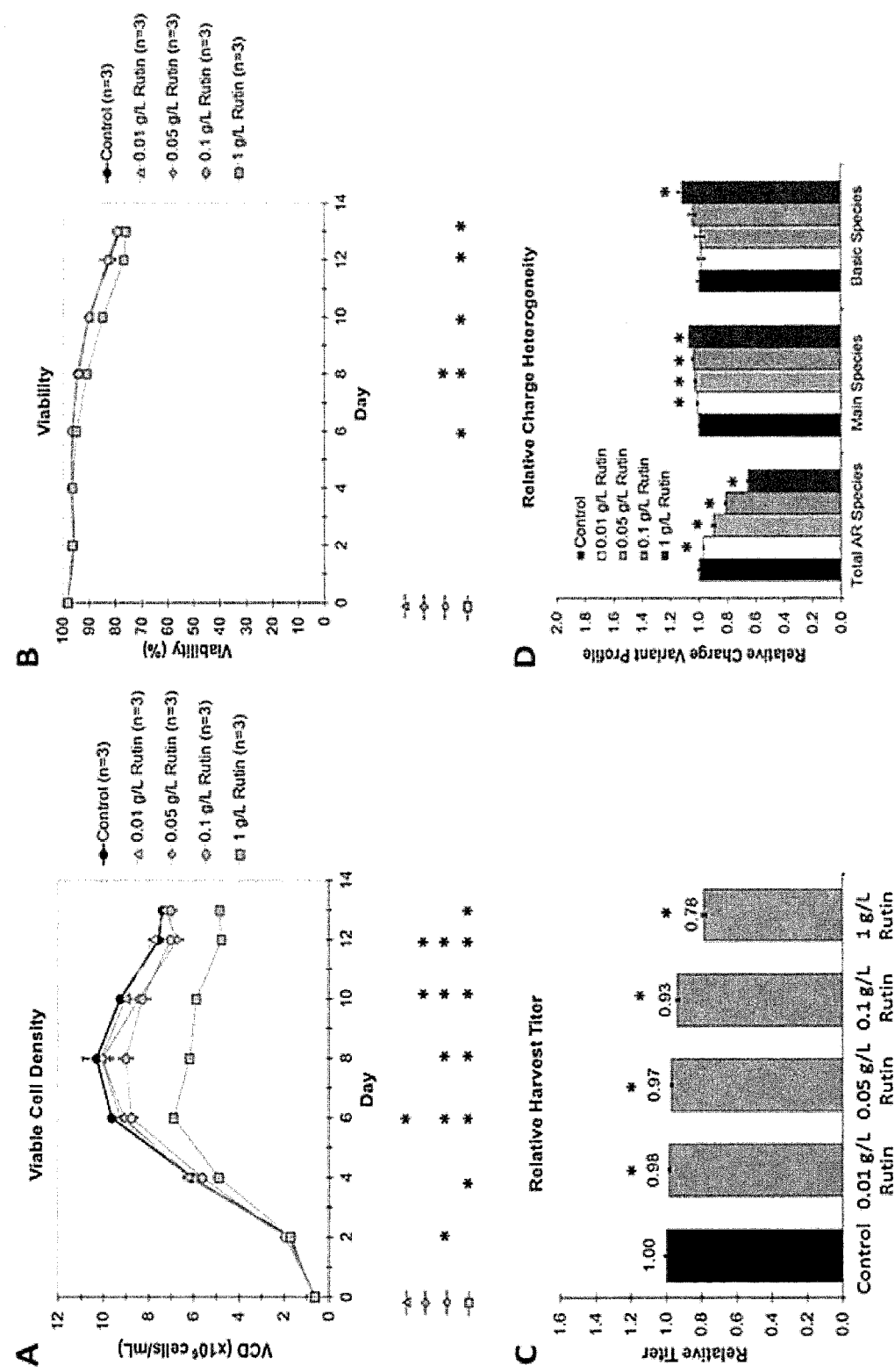
FIG. 14 shows cell culture performance of Cell Line 1 in shake flask culture with rutin supplemented media. A: Viable cell density. B: Cell viability. C: Relative harvest titer compared to unsupplemented control. D: Relative charge variant profile compared to unsupplemented control. (*$p<0.05$ on marked day or process condition indicating a statistically significant difference compared to unsupplemented control).
Figure 15:
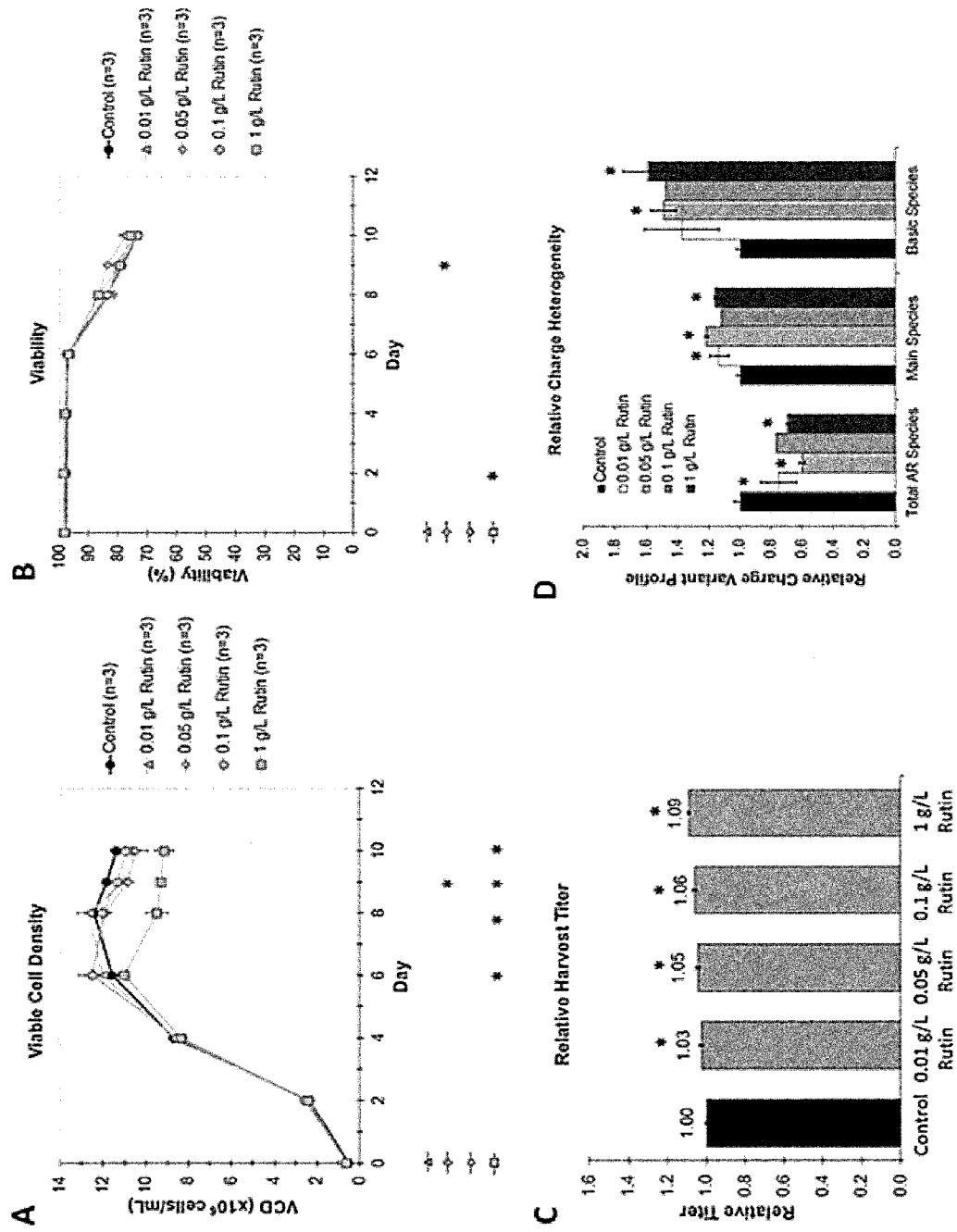
FIG. 15 shows cell culture performance of Cell Line 4 in shake flask culture with rutin supplemented media. A: Viable cell density. B: Cell viability. C: Relative harvest titer compared to unsupplemented control. D: Relative charge variant profile compared to unsupplemented control. (*$p<0.05$ on marked day or process condition indicating a statistically significant difference compared to unsupplemented control).

To evaluate the impact of other bioflavonoids, fed-batch shake flask cultures were initiated with CDFM supplemented with multiple concentrations of rutin. Cell growth, viability, as well as titers and acidic species variants were measured and shown in FIGS. 14 and 15, respectively.

From the cell growth curves of Cell Line 1, one can see that over a wide range of concentrations there was not a significantly adverse impact on culture performance. However, at rutin concentrations above 0.05 g/L in the CDFM, cell growth was adversely impacted. Peak VCD values decreased from $10.3 \times 10^6$ cells/mL for the unsupplemented control down to $9.0 \times 10^6$ cells/mL and $6.9 \times 10^6$ cells/mL for the 0.1 and 1.0 g/L supplemented cultures, respectively. Cell viability results were also very comparable across the duration of each of the cultures. Only the 1 g/L rutin condition demonstrated a reduction in viability, with harvest values dropping to 76% compared to 79% for the unsupplemented control; only a nominal decrease. Harvest titers also demonstrated a nominal decrease across the range of tested concentrations. From 0.01 g/L to 0.1 g/L rutin there was only a drop in relative titer of 0.98 to 0.93, respectively. The 1 g/L condition demonstrated the largest drop in relative titer to 0.78, which was statistically significant.

Upon measurement of the acidic species variants on Antibody 1 from the various cultures, it was found that in each of the evaluated cases, there was a significant drop in acidic species variants. The magnitude of the drop was directly proportional to the amount of rutin in the feed media. The ratio of the acidic region from each of these cultures to the unsupplemented control dropped from 0.97 with the 0.1 g/L rutin culture to 0.65 for the 1 g/L rutin culture. The decrease in total AR was concomitant with an increase the levels of the main and basic species.

From the cell growth curves of Cell Line 4 one can see that over a wide range of concentrations there was not a significantly adverse impact on culture performance. However, at rutin concentrations above 0.1 g/L in the CDFM, cell growth was adversely impacted. Peak VCD values decreased from $12.4 \times 10^6$ cells/mL for the unsupplemented control down to $11.0 \times 10^6$ cells/mL for the 1.0 g/L supplemented cultures, respectively. Cell viability results were also very comparable across the duration of each of the cultures, with the measured values being essentially superimposable against each other. In contrast to Cell Line 1, harvest titers actually increased across the range of tested concentrations. From 0.01 g/L to 0.1 g/L rutin there was a statistically significant increase in relative titer of 1.03 to 1.09 g/L, respectively. Upon measurement of the acidic species variants on DVD 1 from the various cultures, it was found that in each of the evaluated cases, there was a significant drop in acidic species variants. The magnitude of the drop was directly proportional to the amount of rutin in the feed media. The ratio of the acidic region from each of these cultures to the unsupplemented control dropped from 0.75 with the 0.1 g/L rutin culture to 0.69 for the 1 g/L rutin culture. The decrease in total AR was concomitant with an increase the levels of the main and basic species.

These results suggest that various bioflavonoids, such as EGCG, are capable of significantly reducing the overall levels of acidic species on recombinant proteins. However, care must be taken to choose a particular supplementation concentration to ensure that the resulting drop in acidic species does not come at the expense of the resulting process performance, which is also likely cell line dependent.

Figure 16:
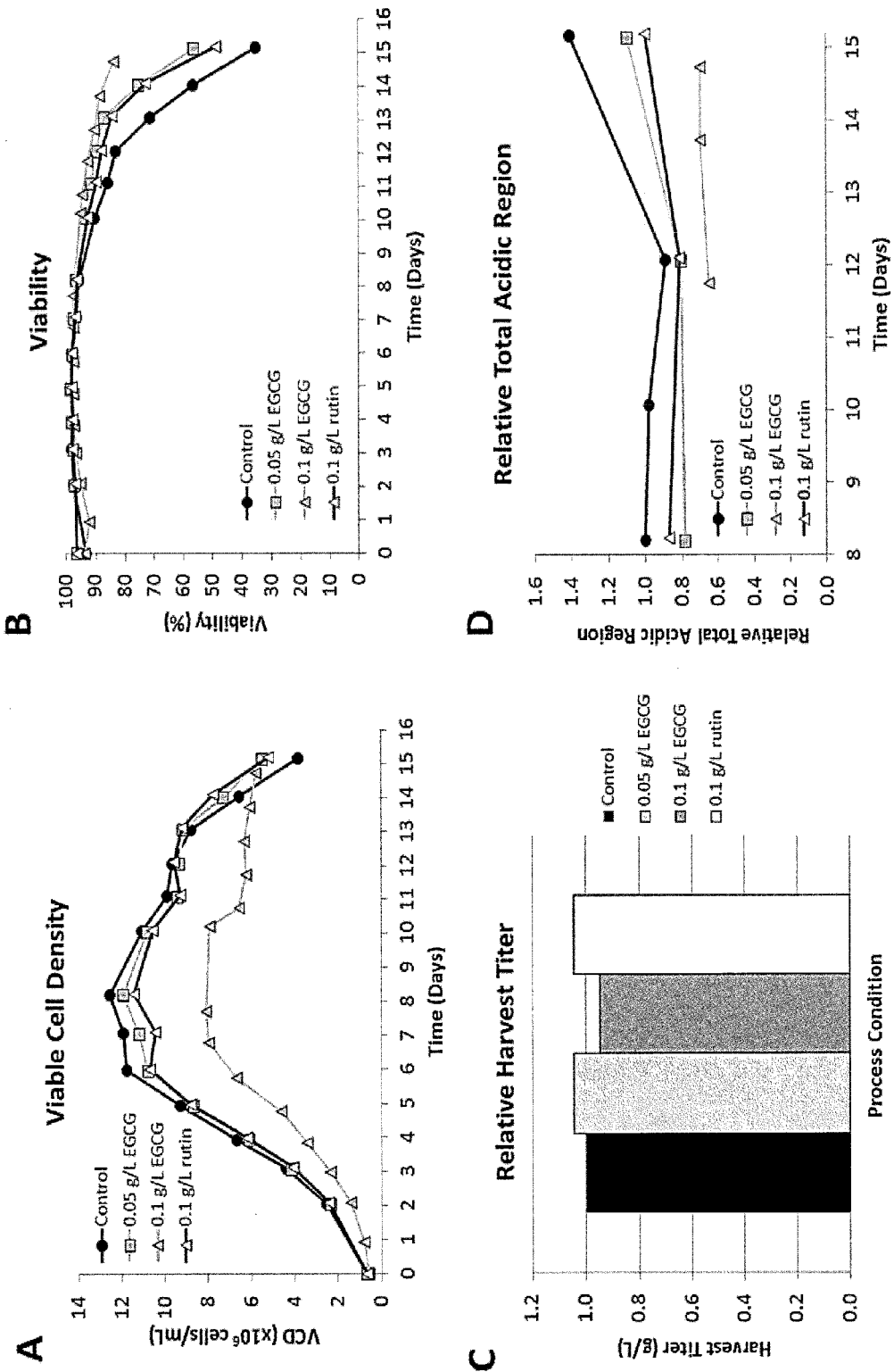
FIG. 16 shows Cell culture performance of Cell Line 1 in laboratory-scale bioreactor cultures with rutin and EGCG supplemented media. A: Viable cell density. B: Cell viability. C: Relative harvest titer compared to unsupplemented control. D: Time course profile of relative acidic region. (Relative acidic region=ratio of measured experimental value to the Day 8 value of the unsupplemented control).

Cell Line 1 was also evaluated in laboratory-scale fedbatch cultures with the feed media supplemented with various bioflavonoids. The resulting impact on cell culture process performance is shown in FIG. 16. Compared to the control condition with no bioflavonoid supplementation, those cultures which were fed with CDFM with 0.05 g/L EGCG and 0.1 g/L rutin exhibited a comparable cell growth with peak viable cell densities reaching approximately $12 \times 10^6$ cells/mL on Day 8 of the cultures. Cell viabilities were above 90% for the majority of the culture duration, with the bioflavonoid supplemented cultures demonstrating a higher cell viabilty throughout the terminal stages of the cultures. Cell growth performance was slightly different however with the 0.1 g/L EGCG supplemented condition. Similar to the shake flask studies, at 0.1 g/L EGCG in the CDFM, the associated cell growth profile was lower than the unsupplemented control culture, however the cell viability remained high. All cultures were able to be successfully harvested on Day 15 post-inoculation. The harvest titers measured from the evaluated cultures were all similar, with the 0.05 g/L EGCG and 0.1 g/L rutin conditions even outperforming the control condition by a nominal amount.

The acidic species profile for the 0.05 g/L and 0.1 g/L EGCG CDFM supplemented cultures, as well as the 0.1 g/L rutin supplemented culture all demonstrated lower levels compared to the unsupplemented CDFM control. This decrease was observed as early as Day 8 of the cultures, and became even more pronounced by the time the cultures were harvested on Day 15. Amongst the evaluated conditions, 0.1 g/L EGCG performed the best with a relative total AR of 0.69. The 0.1 g/L rutin CDFM supplemented culture performed well with a relative total AR of 1.00, which was similar to the 0.05 g/L EGCG condition with a relative total AR of 1.10.

Similar to the results from the shake flask cultures, a concentration-dependent drop in acidic species was observed as the bioflavonoid concentrations were increased in the CDFM. A large fraction of the total acidic species appears between Days 12 and 15 in the unsupplemented control condition. Upon bioflavonoid exposure, this late stage culture increase in acidic species was significantly mitigated. Overall, rutin is very effective in reducing overall AR levels. However, EGCG appears to be slightly more effective, with higher concentration resulting in more decrease in total AR. Rutin demonstrated results on par with those of EGCG, but only when the EGCG concentration was dropped to a lower concentration.

The exact molecular mechanism under which these bioflavonoids exert their effects on total AR is not known. It has been shown that presence of reactive oxygen species (ROS) may impact the physiochemical attributes of expressed proteins. See Klaunig et al. (2010). Bioflavonoids and their pro-oxidant and antioxidant activities, may affect overall ROS levels and prevent their late-stage culture increase. By preventing ROS levels from reaching significantly high levels as the cells are dying in late-stage culture, bioflavonoids may be potentially impacting the subsequent levels of acidic species charge variants. Upon inspection of the weak cation exchange chromatograms of purified Antibody 1, and in particular, the acidic species region, it was readily apparent that the entire chromatogram region of the acidic region decreased upon the cultures supplemented with a bioflavonoid. Since acidic species variants have been shown by previous researchers to be comprised of a mixture of various modifications, it can be concluded that these bioflavonoids are impacting a diverse mixture of different charge variants.

The tested bioflavonoids did not show an adverse impact on overall cell culture performance over a wide range of concentrations. However, once the concentrations of the bioflavonoids exceed a critical level, lower cell growth was observed. For EGCG, concentration of 0.125 g/L was the turning point at which the peak viable cell density of Cell Line 1 began to drop lower than the unsupplemented control conditions. For rutin, concentrations higher than 0.05 g/L and 0.1 g/L were found to be the point at which the peak viable cell densities dropped lower than the unsupplemented control conditions for Cell Lines 1 and 2, respectively. Cell viability results for the most part remained similar throughout the duration of the bioflavonoid supplemented cultures compared to the unsupplemented control cultures. Even in those instances in which the bioflavonoid concentrations were very high, cell viability results were only nominally lower as compared to the control cultures.

Recombinant protein productivity was also only nominally impacted through the culture supplementation of these bioflavonoids up to 0.2 g/L for EGCG and rutin. At higher concentrations, there was a noticeable drop in overall titers. For the EGCG supplemented cultures, harvest titers dropped by at most 8% for EGCG concentrations up to 0.1 g/L. At higher concentrations, including 0.2 g/L, EGCG dropped harvest titers by approximately 28%. For the rutin supplemented cultures, harvest titers dropped by at most 22% for Cell Line 1 fed with CDFM supplemented to 1 g/L. At this same rutin concentration, harvest titers actually increased by 9% for Cell Line 4. Thus, different cell line backgrounds may also have an impact on the responses towards these bioflavonoids. Some cell lines may be more sensitive than others to the same bioflavonoid.

The present disclosure is not to be limited in scope by the specific embodiments described herein. Indeed, various modifications of the invention in addition to those described herein will become apparent to those skilled in the art from the foregoing description and the accompanying figures. Such modifications are intended to fall within the scope of this disclosure and the claims.

REFERENCES

The contents of all cited references (including literature references, patents, patent applications, and websites) that may be cited throughout this application or listed below are hereby expressly incorporated by reference in their entirety for any purpose into the present disclosure. The disclosure may employ, unless otherwise indicated, conventional techniques of immunology, molecular biology and cell biology, which are well known in the art.

The present disclosure also incorporates by reference in their entirety techniques well known in the field of molecular biology and drug delivery. These techniques include, but are not limited to, techniques described in the following publications:

1. Liu, H., et al., Heterogeneity of monoclonal antibodies. J Pharm Sci, 2008. 97(7): p. 2426-47.
2. Walsh, C. T., Posttranslational Modification of Proteins: Expanding Nature's Inventory2006: Roberts and Company.
3. Du, Y., et al., Chromatographic analysis of the acidic and basic species of recombinant monoclonal antibodies. MAbs, 2012. 4(5): p. 578-85.
4. Pardridge, W. M., et al., Cationization of a monoclonal antibody to the human immunodeficiency virus REV protein enhances cellular uptake but does not impair antigen binding of the antibody. Immunol Lett, 1994. 42(3): p. 191-5.
5. Pardridge, W. M., et al., Cationized hyperimmune immunoglobulins: pharmacokinetics, toxicity evaluation and treatment of human immunodeficiency virus-infected human-peripheral blood lymphocytes-severe combined immune deficiency mice. J Pharmacol Exp Ther, 1996. 276(1): p. 246-52.
6. Huang, L., et al., In vivo deamidation characterization of monoclonal antibody by LC/MS/MS. Anal Chem, 2005. 77(5): p. 1432-9.
7. Vlasak, J., et al., Identification and characterization of asparagine deamidation in the light chain CDR1 of a humanized IgG1 antibody. Anal Biochem, 2009. 392(2): p. 145-54.
8. Banks, D. D., et al., The effect of sucrose hydrolysis on the stability of protein therapeutics during accelerated formulation studies. J Pharm Sci, 2009. 98(12): p. 4501-10.
9. Khawli, L. A., et al., Charge variants in IgG1: Isolation, characterization, in vitro binding properties and pharmacokinetics in rats. MAbs, 2010. 2(6): p. 613-24.
10. Abu-Absi, S. F., et al., Defining process design space for monoclonal antibody cell culture. Biotechnol Bioeng, 2010. 106(6): p. 894-905.
11. Lambert, J. D. and R. J. Elias, The antioxidant and pro-oxidant activities of green tea polyphenols: a role in cancer prevention. Arch Biochem Biophys, 2010. 501(1): p. 65-72.
12. Forester, S. C. and J. D. Lambert, The role of antioxidant versus pro-oxidant effects of green tea polyphenols in cancer prevention. Mol Nutr Food Res, 2011. 55(6): p. 844-54.
13. Halliwell, B., Are polyphenols antioxidants or pro-oxidants? What do we learn from cell culture and in vivo studies? Arch Biochem Biophys, 2008. 476(2): p. 107-12.
14. Bellion, P., et al., Formation of hydrogen peroxide in cell culture media by apple polyphenols and its effect on antioxidant biomarkers in the colon cell line HT-29. Mol Nutr Food Res, 2009. 53(10): p. 1226-36.

15. Long, L. H., M. V. Clement, and B. Halliwell, Artifacts in cell culture: rapid generation of hydrogen peroxide on addition of (−)-epigallocatechin, (−)-epigallocatechin gallate, (+)-catechin, and quercetin to commonly used cell culture media. Biochem Biophys Res Commun, 2000. 273(1): p. 50-3.
16. Wu, C., et al., Simultaneous targeting of multiple disease mediators by a dual-variable-domain immunoglobulin. Nat Biotechnol, 2007. 25(11): p. 1290-7.
17. Klaunig, J. E., L. M. Kamendulis, and B. A. Hocevar, Oxidative stress and oxidative damage in carcinogenesis. Toxicol Pathol, 2010. 38(1): p. 96-109.
18. Zhou, L. and R. J. Elias, Factors influencing the antioxidant and pro-oxidant activity of polyphenols in oil-in-water emulsions. J Agric Food Chem, 2012. 60(11): p. 2906-15.
19. National Center for Biotechnology Information. PubChem Compound Database; CID=5280805. Available from: https://pubchem.ncbi.nlm.nih.gov/summary/summary.cgi?cid=5280805&loc=ec_rcs (Accessed 04/18/14).
20. National Center for Biotechnology Information. PubChem Compound Database; CID=442428. Available from: https://pubchem.ncbi.nlm.nih.gov/summary/summary.cgi?cid=442428&loc=ec_rcs (Accessed 04/18/14).
21. National Center for Biotechnology Information. PubChem Compound Database; CID=5280961. Available from: https://pubchem.ncbi.nlm.nih.gov/summary/summary.cgi?cid=5280961&loc=ec_rcs (Accessed 04/18/14).
22. National Center for Biotechnology Information. PubChem Compound Database; CID=65064. Available from: https://pubchem.ncbi.nlm.nih.gov/summary/summary.cgi?cid=65064&loc=ec_rcs (Accessed 04/18/14).

EQUIVALENTS

The disclosure may be embodied in other specific forms without departing from the spirit or essential characteristics thereof. The foregoing embodiments are therefore to be considered in all respects illustrative rather than limiting of the disclosure. Scope of the disclosure is thus indicated by the appended claims rather than by the foregoing description, and all changes that come within the meaning and range of equivalency of the claims are therefore intended to be embraced herein.

We claim:

1. A composition comprising a chemically-defined medium (CDM) and a bioflavonoid selected from the group consisting of epigallocatechin gallate (EGCG), rutin, naringin, and genistein, wherein said bioflavonoid is present in said composition at a concentration ranging from about 0.001 g/L to about 0.2 g/L.

2. The composition of claim 1, wherein said composition is in a liquid form and is capable of culturing cells with or without dilution.

3. The composition of claim 1, wherein said composition is in a solid form and is capable of being reconstituted with water for culturing cells.

4. A composition comprising a chemically-defined medium (CDM), a bioflavonoid selected from the group consisting of epigallocatechin gallate (EGCG), rutin, naringin, and genistein, and a plurality of recombinant cells, wherein said plurality of recombinant cells are capable of expressing a recombinant protein.

5. The composition of claim 4, wherein said recombinant protein is an anti-TNF-alpha antibody said anti-TNF-alpha antibody having reduced levels of acidic species as compared to anti-TNF-alpha antibody produced in cell culture without said bioflavonoid.

6. The composition of claim 4, wherein said bioflavonoid is a member selected from the group consisting of epigallocatechin gallate (EGCG), rutin, naringin, genistein and combination thereof.

7. The composition of claim 6, wherein said bioflavonoid is epigallocatechin gallate (EGCG), wherein said epigallocatechin gallate is present in said composition at a concentration ranging from about 0.001 g/L to about 0.2 g/L.

8. The composition of claim 7, wherein the concentration of said epigallocatechin gallate in said composition is from about 0.01 g/L to about 0.1 g/L.

9. The composition of claim 6, wherein said bioflavonoid is rutin, in said composition at a concentration ranging from about 0.001 g/L to about 0.2 g/L.

10. The composition of claim 6, wherein said bioflavonoid is naringin, in said composition at a concentration ranging from about 0.001 g/L to about 2 g/L.

11. The composition of claim 6, wherein said bioflavonoid is genistein, in said composition at a concentration ranging from about 0.001 g/L to about 0.2 g/L.

12. A method for producing a polypeptide, the method comprising culturing a plurality of cells in a culture medium comprising a bioflavonoid, wherein at least one of said plurality of cells is capable of expressing said polypeptide, wherein said bioflavonoid is selected from the group consisting of epigallocatechin gallate (EGCG), rutin, naringin, and genistein, and said bioflavonoid is present in said culture medium at a concentration ranges from about 0.001 g/L to about 0.2 g/L.

13. The method of claim 12, wherein said polypeptide is an antibody.

14. The method of claim 12, wherein said bioflavonoid is epigallocatechin gallate (EGCG), said EGCG being present in the culture medium at a concentration of from about 0.001 g/L to about 0.2 g/L.

15. The method of claim 14, wherein said EGCG is present in the culture medium at a concentration of from about 0.01 g/L to about 0.1 g/L.

16. The method of claim 12, wherein said bioflavonoid is rutin, said rutin being present in the culture medium at a concentration of from about 0.001 g/L to about 0.2 g/L.

17. The method of claim 12, wherein said bioflavonoid is naringin, said naringin being present in the culture medium at a concentration of from about 0.001 g/L to about 2 g/L.

18. The method of claim 12, wherein said bioflavonoid is genistein, said genistein being present in the culture medium at a concentration of from about 0.001 g/L to about 0.2 g/L.

19. The method of claim 12, wherein said bioflavonoid is added to the culture medium in a substantially pure form.

20. The method of claim 12, wherein said bioflavonoid is added to the culture medium as a crude extract prepared from a plant or parts thereof.

21. The method of claim 12, wherein said polypeptide is an anti-TNF-alpha antibody.

22. The method of claim 12, wherein said polypeptide is an antibody comprising dual variable domains (DVD).

* * * * *